(12) United States Patent
Florkey et al.

(10) Patent No.: US 6,984,359 B2
(45) Date of Patent: Jan. 10, 2006

(54) STERILIZER INCLUDING AIR PURGING SYSTEM AND PRESSURE ACTUATED DOOR SEAL

(75) Inventors: Edward J. Florkey, Vandalia, OH (US); Ronald A. Gatchell, Tipp City, OH (US); Richard L. Jones, Eaton, OH (US); Michael J. Coyle, Huber Heights, OH (US); Philip M. Stewart, Greenville, OH (US)

(73) Assignee: Midmark Corporation, Versailles, OH (US)

( * ) Notice: Subject to any disclaimer, the term of this patent is extended or adjusted under 35 U.S.C. 154(b) by 572 days.

(21) Appl. No.: 09/990,130

(22) Filed: Nov. 21, 2001

(65) Prior Publication Data

US 2002/0085945 A1    Jul. 4, 2002

Related U.S. Application Data

(63) Continuation-in-part of application No. 09/268,599, filed on Mar. 15, 1999, now abandoned.

(51) Int. Cl.
*A61L 2/08* (2006.01)

(52) U.S. Cl. ............................ 422/3; 49/477.1; 49/394; 422/26; 422/292; 422/295; 422/296; 422/307

(58) Field of Classification Search .................. 422/26, 422/3, 292, 295, 296, 307; 49/477.1, 394
See application file for complete search history.

(56) References Cited

U.S. PATENT DOCUMENTS

| | | | |
|---|---|---|---|
| 3,814,901 A | 6/1974 | Morhack | 219/401 |
| 3,826,612 A | 7/1974 | Black | 21/94 |
| 4,261,950 A | 4/1981 | Bainbridge et al. | 422/26 |
| D264,123 S | 4/1982 | Brendgord et al. | D24/9 |
| D264,124 S | 4/1982 | Brendgord et al. | D24/9 |
| 4,426,358 A | 1/1984 | Johansson | 422/112 |
| 4,441,724 A * | 4/1984 | Taylor | 277/640 |

(Continued)

Primary Examiner—Krisanne Jastrzab
(74) Attorney, Agent, or Firm—Wood, Herron & Evans, LLP

(57) ABSTRACT

A sterilizer including a sterilization chamber for receiving articles to be sterilized and a door supported on a horizontal pivot at an access opening of the sterilizer chamber. The door includes a seal plate and a resilient seal member supported on the seal plate wherein the seal member includes an annular lip extending transversely to the plane of the seal plate. The lip extends into the sterilizer chamber wherein pressure within the chamber exerts a force biasing an opposing surface of the lip into engagement with an inner surface of the chamber. The sterilizer door is movable between a fully closed and a fully open position and includes a mechanism for holding the door in a partially open position. In the partially open position, the lip extends into contact with a surface of the sterilizer chamber to thereby form a bridge between the door and chamber and prevent condensation from dripping down away from the chamber and door. A controller is provided for controlling sterilization cycles and actuates the door to move to the partially open position at the end of a sterilization cycle. In addition, a pressure actuated lock is provided for preventing the door from opening when the chamber is pressurized. The controller further automatically controls purging of air from the sterilizer chamber during a steam generation mode of a sterilization cycle wherein the controller senses the temperature and pressure during the sterilization cycle, and in response thereto, opens a purge valve to release air when the conditions within the sterilizer deviate by a predetermined amount from preset conditions monitored by the controller.

37 Claims, 17 Drawing Sheets

U.S. PATENT DOCUMENTS

| | | |
|---|---|---|
| 4,848,031 A | 7/1989 | Yamagishi et al. ............ 49/280 |
| 4,951,693 A * | 8/1990 | Archambault ........... 134/57 DL |
| D330,771 S | 11/1992 | Chaney et al. ............. D24/217 |
| 5,223,229 A | 6/1993 | Brucker ...................... 422/116 |
| 5,313,738 A * | 5/1994 | Thakur et al. ................ 49/394 |
| D347,696 S | 6/1994 | Tominaga .................. D24/217 |
| 5,424,047 A * | 6/1995 | Zwingenberger et al. ... 422/296 |
| 6,117,687 A * | 9/2000 | Hugh ......................... 436/183 |
| D433,147 S | 10/2000 | Florkey et al. ............. D24/217 |

* cited by examiner

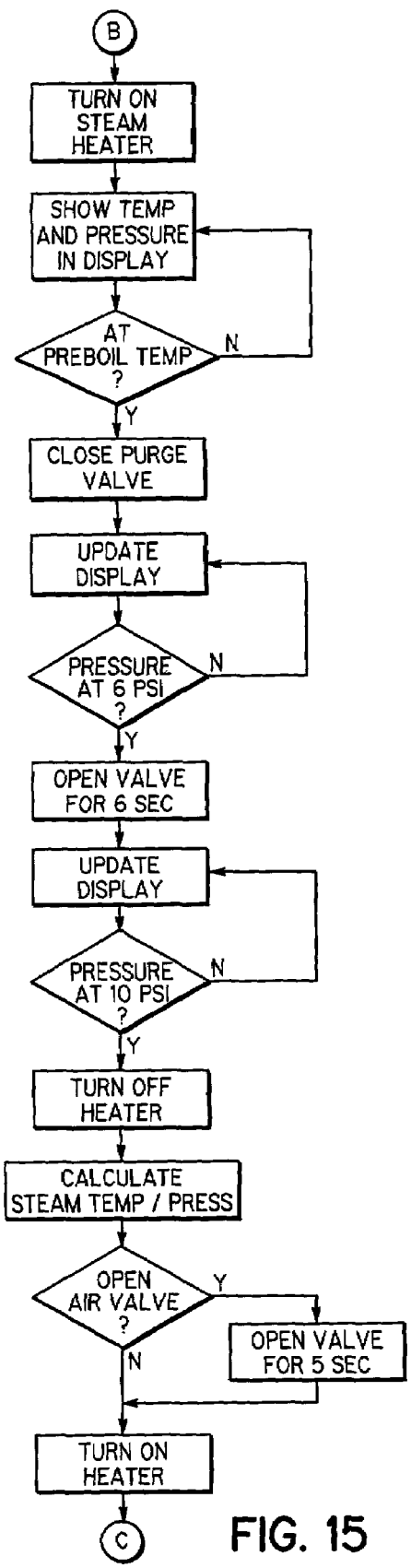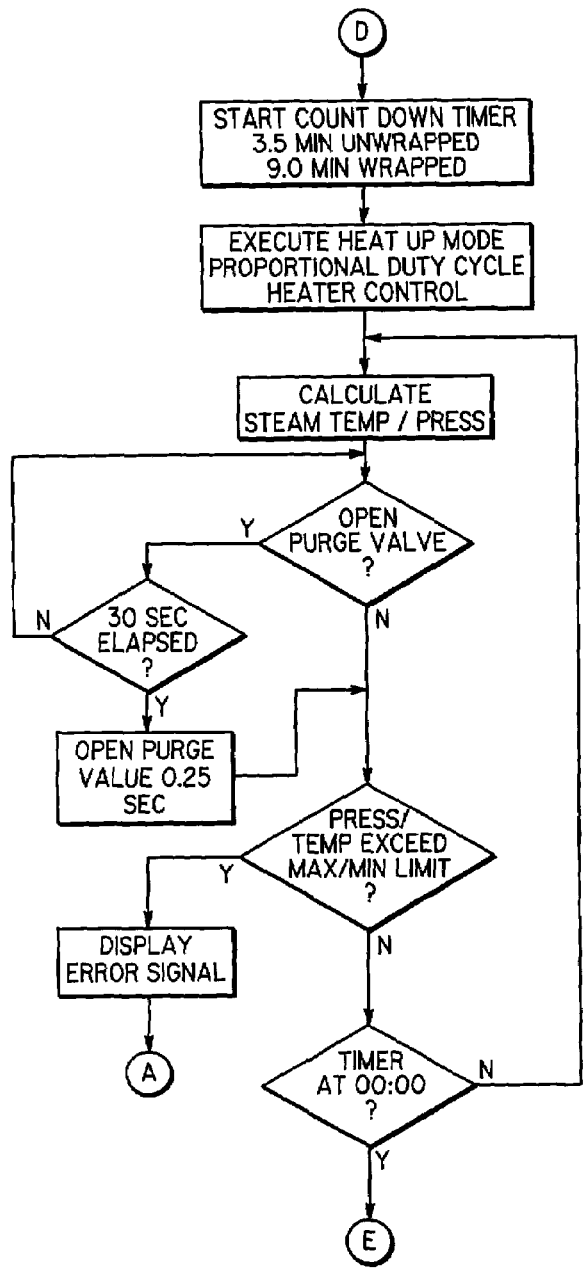
FIG. 15
FIG. 17

STERILIZER INCLUDING AIR PURGING SYSTEM AND PRESSURE ACTUATED DOOR SEAL

CROSS REFERENCE TO RELATED APPLICATION

This application is a continuation-in-part of U.S. Patent application Ser. No. 09/268,599 filed Mar. 15, 1999 entitled "Sterilizer Including Air Purging System and Pressure Actuated Door Seal" (now abandoned), the disclosure of which is hereby incorporated herein by reference in its entirety.

BACKGROUND OF THE INVENTION

The present invention relates generally to sterilizers and, more particularly, to a sterilizer including a system for purging air to increase the steam content within a sterilizer chamber, and a seal which increases sealing forces with increasing sterilizer chamber pressure.

Sterilizers are widely used to sterilize articles in medical environments and typically employ a steam filled chamber for containing the articles, and rely on subjecting the articles to steam at a predetermined temperature and pressure for a preset period of time. The steam may either be provided by means of a separate steam producing chamber or by supplying water to the sterilizer chamber and heating the chamber until the water evaporates. In either case, the chamber is provided with a heater to elevate the temperature in the chamber and cause an accompanying increase in pressure such that sterilization of the articles is effected.

To ensure proper sterilization, it is desirable to replace any air in the sterilizer chamber with steam. This has been accomplished in prior art devices by applying a vacuum to the chamber to draw the air out or, in an alternative approach, a vent is opened as the chamber fills with steam to permit the air in the chamber to be displaced and pushed out of the chamber by the steam. For example, U.S. Pat. No. 3,826,612 to Black discloses an autoclave or sterilizer in which a steam generating chamber delivers steam to an autoclaving chamber wherein a temperature responsive valve is in fluid communication with the autoclaving chamber and permits air to pass out of the chamber, and which closes automatically upon an appreciable rise in the temperature as a result of steam flowing from the chamber through the valve.

In addition, table top sterilizers conventionally have doors pivoted to one side such that the door swings upon a vertical axis. In a typical use of such a sterilizer, the door is partially opened after release of pressure within the chamber, and before the articles in the chamber have cooled, to permit any moisture remaining on the articles to evaporate more quickly as the moisture content within the chamber decreases. For example, U.S. Pat. No. 5,223,229 to Brucker, and assigned to the assignee of the present invention, discloses a sterilizing apparatus having a door mounted on a vertical axis and wherein the door is automatically actuated to open a small amount when the pressure within the sterilizer chamber decreases to a predetermined level to facilitate cooling and drying of articles within the chamber.

The cooling process results in condensation and dripping of moisture in the area of the gap between the door and the chamber opening, and there is a need to reduce the amount of moisture lost in the form of condensation from the sterilizer. In addition, there is a need for an improved sterilization process which increases the amount of steam relative to the amount of air contained within the chamber during the sterilization process.

SUMMARY OF THE INVENTION

The present invention provides a sterilizer for providing a heated and pressurized steam environment for sterilizing articles. The sterilizer includes a sterilizing chamber for receiving the articles to be sterilized wherein the chamber includes an inner wall defining a chamber interior for the sterilizer. A planar surface defines a front face of the sterilizer which is formed generally perpendicular to and extending outwardly from the inner wall, and the front face defines a chamber opening for access to the chamber interior.

The sterilizer further includes a door mounted for movement relative to the chamber between a fully closed position wherein the door is in engagement with the front face, and a fully open position wherein an operator may access the chamber interior for insertion and removal of articles therein. The door is supported on a horizontal pivot axis permitting the upper end of the door to pivot away from the front face to provide access to the sterilizer chamber.

A resilient seal is supported on and covers an interior surface of the door. The resilient seal includes a lip extending generally perpendicular to the interior surface of the door and located for engagement with the inner wall of the sterilizer chamber when the door is in a fully closed position. Pressure within the sterilizer chamber biases the lip into sealing engagement with the surface of the inner wall such that increased pressure within the chamber increases the sealing force of the lip against the inner wall.

The door is provided with a latch mechanism for cooperating with a catch mechanism associated with the sterilizer chamber wherein the latch mechanism is adapted to hold the door in the fully closed position, as well as in a partially open position intermediate the fully closed and fully open positions. In the partially open position, the lip forms a bridge extending between the inner wall of the sterilizer chamber and the interior surface of the door whereby the lip prevents dripping of condensation from the door and the chamber.

The door further includes a lock having an actuator mechanism which is actuated by pressure within the chamber to lock the latch mechanism and thereby lock the door in the fully closed position. The resilient seal extends inwardly from the lip toward a center portion of the door and provides a flexible cover over the actuator mechanism whereby pressure acting on the resilient seal is transferred to the actuator mechanism to actuate the lock.

A controller is provided for monitoring and controlling the sterilization process of the sterilizer and is connected to temperature and pressure sensors for measuring the temperature and pressure within the chamber interior. A purge valve is provided in fluid communication with the chamber interior and is connected to and energized by the controller to open and purge air from the chamber interior in response to at least one of the temperature and pressure sensor means sensing a predetermined condition within the chamber whereby the percentage of air relative to steam within the chamber is decreased.

In the preferred embodiment, the controller opens the purge valve for a preset period of time if the conditions within the chamber deviate from predetermined saturated steam conditions. Further, the purge valve may be opened a plurality of times as the conditions within the chamber are monitored in order to provide a maximum percentage of steam relative to air within the chamber.

Therefore, it is an object of the present invention to provide a sterilizer incorporating an improved seal between the door and the chamber of the sterilizer.

It is another object of the invention to provide a sterilizer incorporating a pressure actuated lock mechanism for locking the sterilizer door in a closed position when pressure is present within the chamber.

It is yet another object of the invention to provide a sterilizer including an improved system for purging air from the sterilizer to increase the percentage of steam relative to air during a sterilization process.

Other objects and advantages of the invention will be apparent from the following description and the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIGS. 15 and 16 are a flow chart depicting the operation of the sterilizer during a Heat-up Mode of the sterilization process;

FIG. 17 is a flow chart depicting the operation of the sterilizer during a Sterilization Mode of the sterilization process;

DETAILED DESCRIPTION

Figure 1:
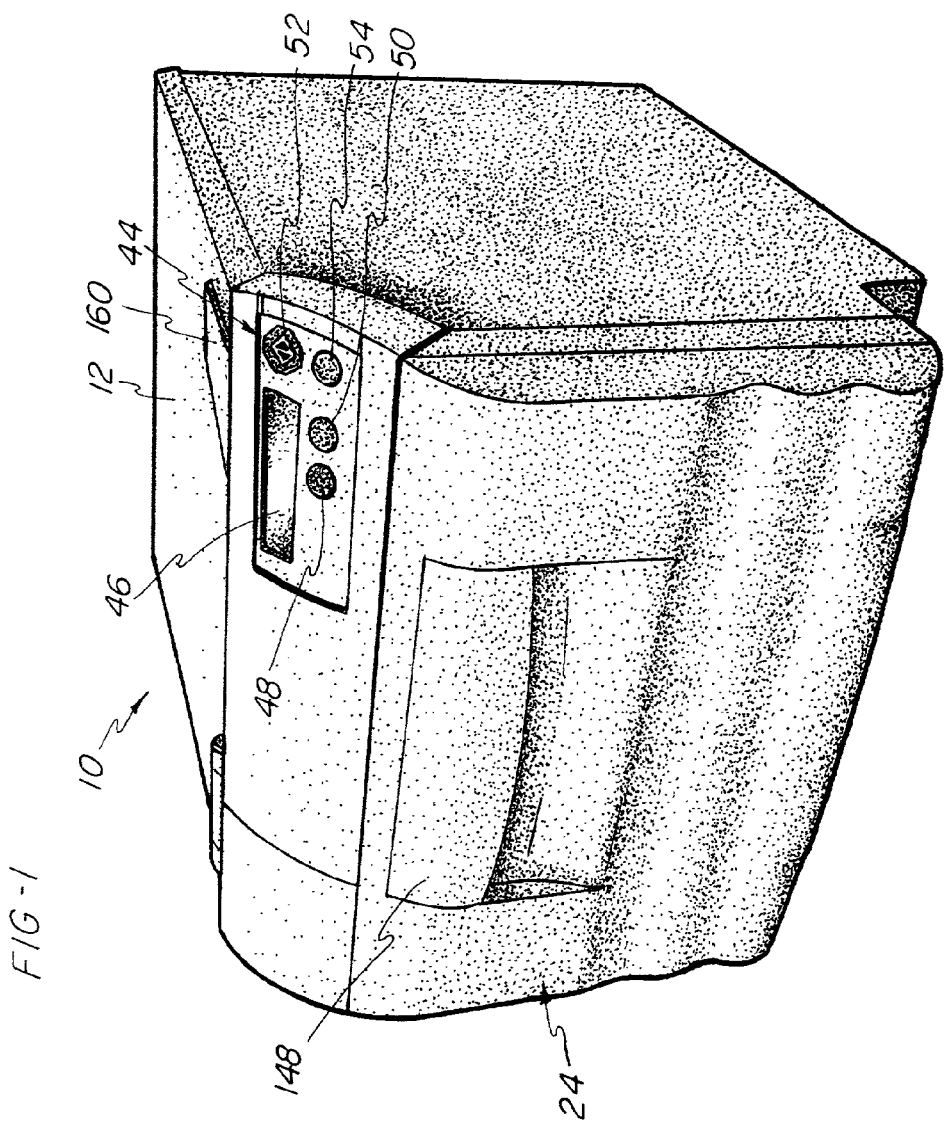
FIG. 1 is a perspective view of the sterilizer of the present intention with the door in a closed position.
Figure 2:
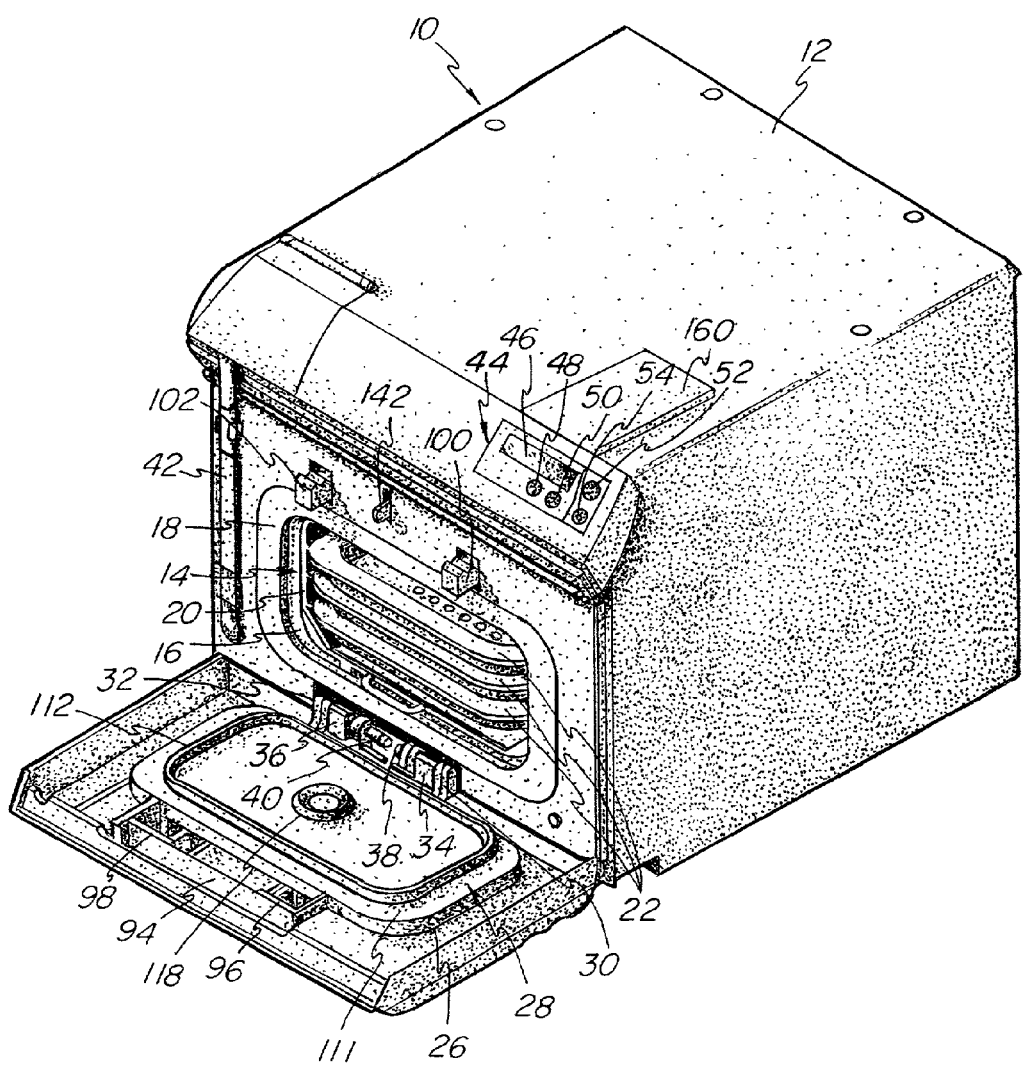
FIG. 2 is a perspective view of the sterilizer with the door in an open position, and illustrating articles positioned within the sterilizer chamber.

Referring initially to FIGS. 1 and 2, the sterilizer 10 of the present invention includes an outer cover 12 within which a sterilizer chamber 14 is enclosed. The sterilizer chamber 14 includes an inner wall 16 defining a chamber interior, and the chamber 14 further includes a planar surface defining a front face 18 formed generally perpendicular to and extending outwardly from the inner wall 16 wherein the front face 18 surrounds and defines a chamber opening for access to the chamber interior. In addition, the chamber interior includes racks 20 for supporting trays 22 containing articles to be sterilized by the sterilizer 10.

A door 24 defines a front portion of the sterilizer 10 and includes a chamber sealing plate 26 (see also FIGS. 7 and 8) to which a resilient seal 28 is attached for engagement with the inner wall 16 and front face 18 of the chamber 14, as will be described further below. The door 24 is supported for pivotal movement relative to the chamber 14 by means of mounting legs 30, 32 rigidly attached to the sealing plate 26, and supported to pivot mounts 34, 36 of the chamber 14 by means of pivot pins 38, 40. Thus, the door 24 of the present sterilizer 10 is mounted for rotation about a lower horizontal axis wherein the upper edge of the door 24 swings away from the chamber 14 to provide access to the chamber interior whereby articles, such as the trays 22, may be inserted or removed.

Positioning of the door 24 in the open position further provides access to view a water level indicator tube 42 which is attached to a water reservoir (not shown) for supplying water to produce steam in the sterilizer chamber 14. The water reservoir for the present sterilizer 10 is similar to that provided in the sterilizer disclosed in U.S. Pat. No. 5,223,229, assigned to the assignee of the present invention, and incorporated herein by reference.

The sterilizer 10 further includes a control panel 44 having a display 46 which indicates the particular cycle selected for the sterilizer 10 and the temperature and exposure time for the selected cycle. In addition, the display 46 provides the operator with messages describing the status of the cycle, including any error messages and the remaining cycle time, as well as temperature and pressure after the cycle reaches a Sterilization Mode.

The control panel 44 also includes control buttons for selecting preprogrammed sterilization processes, including an "unwrapped" button 48 for sterilizing unwrapped instruments according to a preselected sterilization cycle, a "wrapped" button 50 for sterilizing wrapped instruments, a start button 52 for starting the sterilization cycle, and a stop button 54 which, when pressed, will terminate a sterilization cycle currently in progress. The display 46 and control buttons 48, 50, 52, 54 are all connected to a controller 150 (see FIG. 12) which controls operation of the sterilizer.

Figure 3:
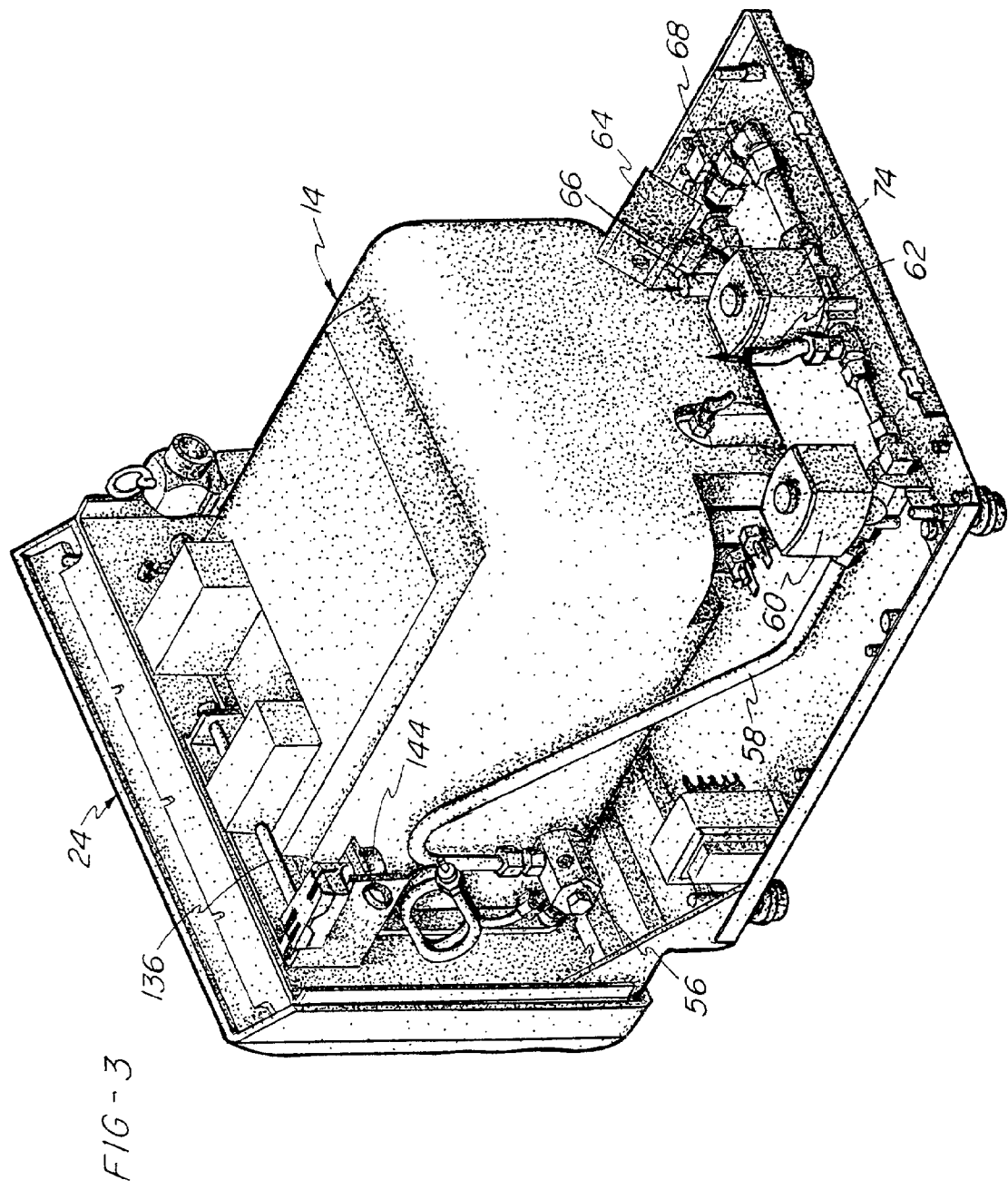
FIG. 3 is a right rear perspective view of the sterilizer with the outer cover removed.
Figure 4:
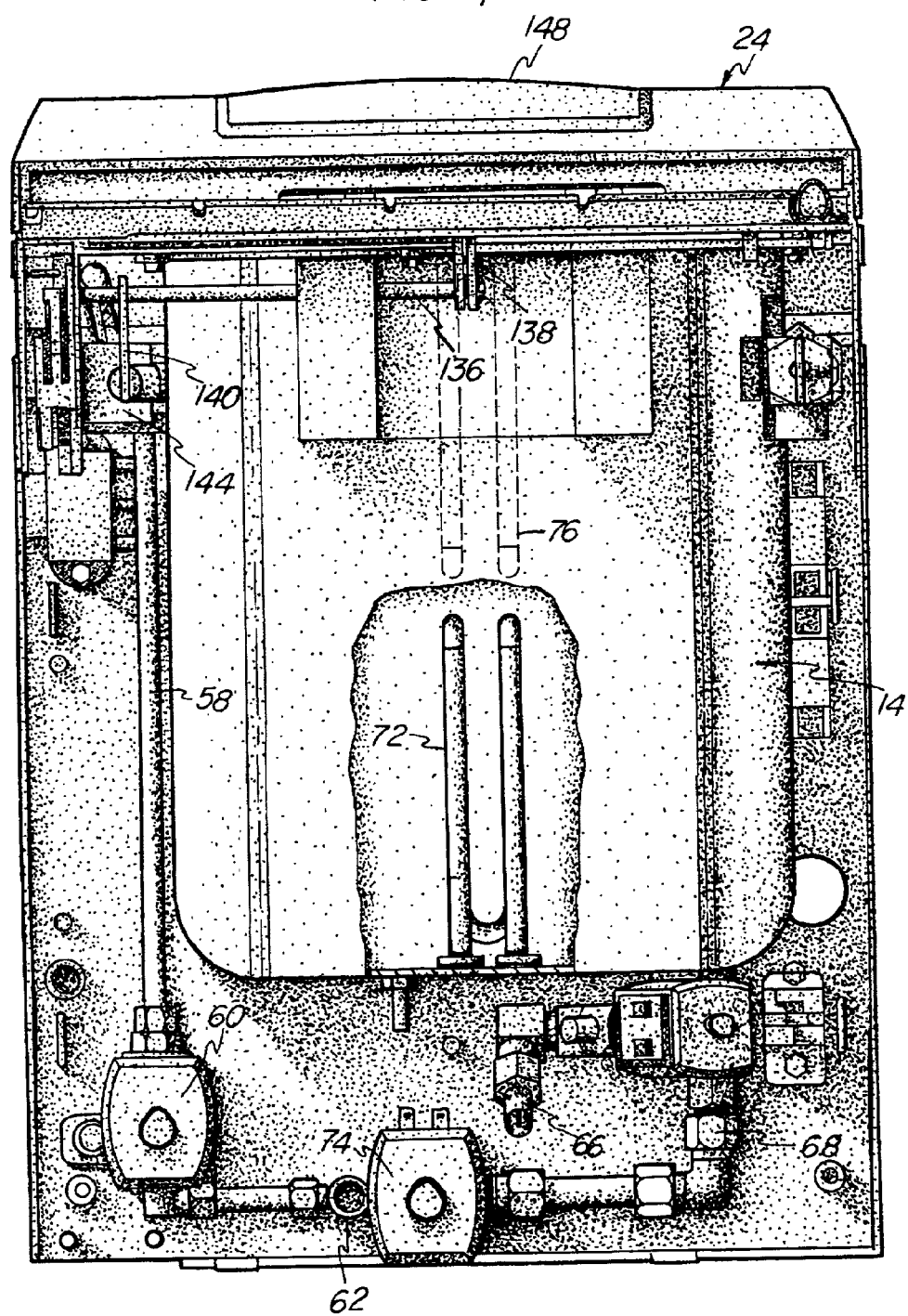
FIG. 4 is a top plan view of the sterilizer with the outer cover removed and with a portion of the sterilizing chamber cut away to show an interior heating element.

Referring to FIGS. 3 and 4, an air vent port 56 is provided in fluid communication with the interior of the chamber 14 for conveying air from the chamber 14 as the chamber 14 is filled with steam. An air vent line 58 extends from the port 56 to a solenoid actuated air or purge valve 60 wherein the purge valve 60 controls flow of air from the air vent line 58 to a condensation line 62 which extends to a condensing coil located within the water reservoir (not shown).

Figure 5:
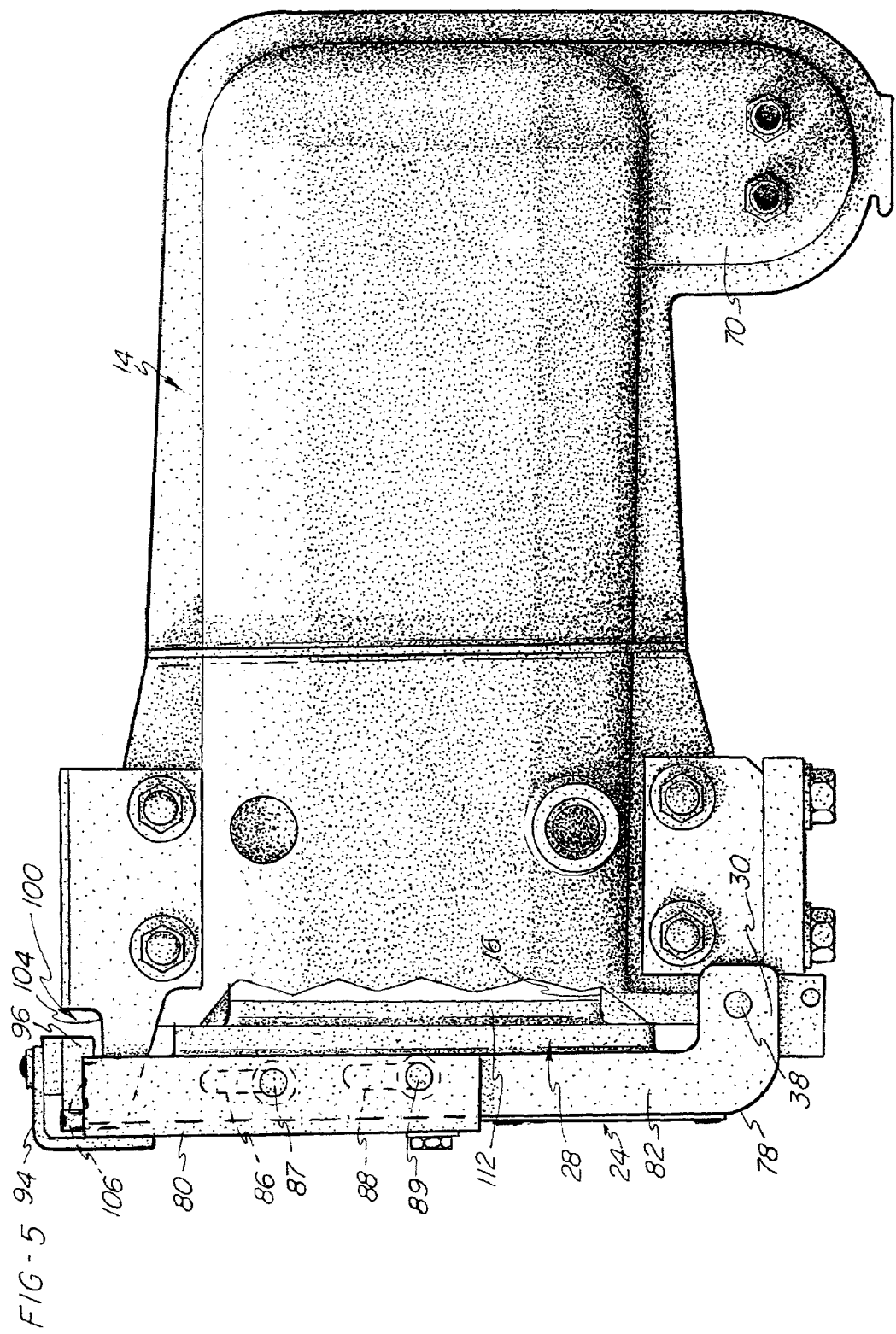
FIG. 5 is a side elevational view of the sterilizer chamber and door illustrating the door in a fully closed position, and with a portion of the chamber cut away to show the seal.
Figure 11:
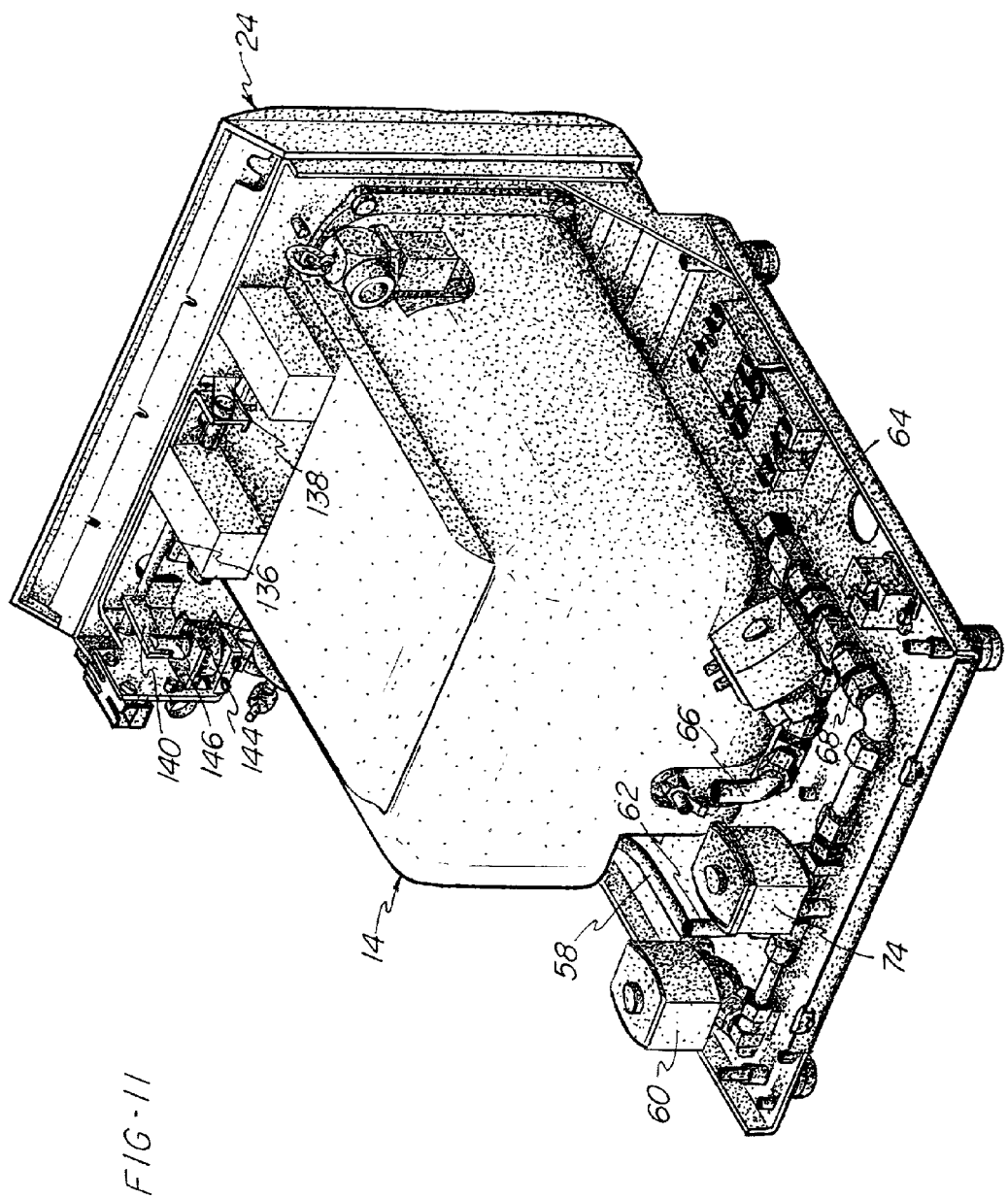
FIG. 11 is a left rear perspective view of the sterilizer with the back cover removed.

A water fill solenoid valve 64 is connected to a water fill passage 66 extending from the water reservoir. The water fill solenoid controls flow of water through a passage 68 (see also FIG. 11) extending in fluid communication with the interior of the chamber 14. The water is supplied to a water basin portion 70 formed in the lower rear portion of the chamber 14 (see also FIGS. 5 and 6). An electric heater element 72 (the steam heater) is located within the basin portion 70 for heating water supplied thereto to thereby form steam within the chamber 14.

A further solenoid valve 74 is provided connected between the passage 68 and the condensation line 62. The solenoid valve 74 is opened at the end of a sterilization cycle to vent steam from the interior of the sterilizer chamber 14 to the condensing coil (not shown) of the water reservoir (not shown).

It should be further noted that an auxiliary heater 76 is provided in the sterilizer chamber 14 in order to facilitate preheating of the chamber 14 prior to sterilization which reduces the time to achieve sterilization temperature, as well as to maintain the temperature of the chamber during the drying of articles after sterilization.

Referring to FIGS. 2 and 5–8, the door 24 is movable between a fully closed position (FIG. 5), where the door 24 is in sealing engagement over the chamber opening 20, and a fully open position (FIG. 2), where the door is fully displaced from the chamber opening 20 to permit insertion and removal of articles to and from the chamber 14. The door 24 includes a pivoted frame 78, including the sealing plate 26 and mounting legs 30, 32. The door 24 further includes a sliding frame or latch mechanism 80 mounted for sliding vertical movement relative to the pivoted frame 78. In particular, the pivoted frame 78 includes vertically extending members 82, 84 wherein the vertically extending members 82, 84 each include a pair of elongated slots 86, 88. The sliding frame 80 includes a pair of vertical guide members 90, 92 positioned over the vertically extending members 82, 84 wherein each guide member 90, 92 includes a pair of vertically spaced pins 87, 89 extending through the slots 86, 88, respectively. The cooperation between the slots 86, 88 and pins 87, 89 maintain the sliding frame 80 in position on the pivoted frame 78 while permitting vertical movement of the sliding frame 80 in a plane parallel to the plane of the pivoted frame 78.

A horizontal frame member 94 is supported at upper ends of the vertical guide members 90, 92 and maintains the desired spacing between the upper ends of the vertical guide members 90, 92. The upper ends of the vertical guide members 90, 92 further include latch members 96, 98 defined by flange portions extending downwardly or away from the horizontal support member 94. The latch members 96, 98 engage within respective stepped catch members 100, 102 wherein each catch member 100, 102 includes a first step portion 104 defining a fully closed position of the sterilizer door 24, and a second step portion 106 defining a partially open position for the door 24 intermediate the fully closed and the fully open positions.

Figure 10:
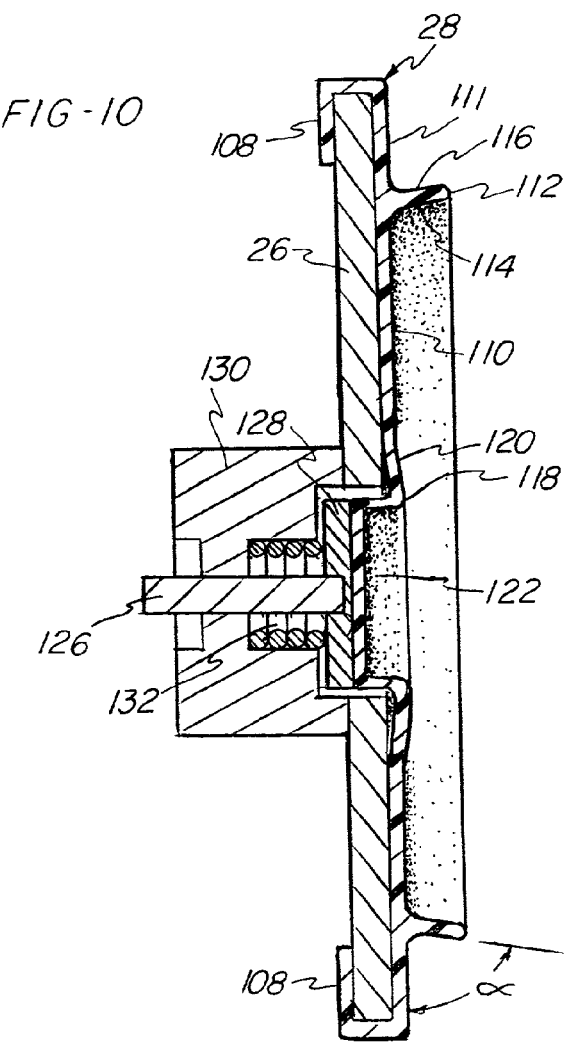
FIG. 10 is a cross-sectional view in side elevation of the resilient seal on the seal plate and showing the pressure lock in a locked position.

Referring further to FIG. 10, the resilient seal 28 is mounted to the seal plate 26 of the door 24 by flange portions 108 extending around the peripheral edge of the sealing plate 26. Further, the resilient seal 28 includes a generally planar portion 110 extending over substantially the entire inner surface of the sealing plate 26 including a lip portion 112 extending outwardly from and transverse to the planar portion 110. The lip portion 112 is defined as an annular member defining a shape corresponding to the shape of the access opening of the chamber 14. Further, the lip portion 112 comprises a thin wall member having a height approximately five times greater than its width, and defining an inner surface 114 and an outer surface 116. Also, the lip portion 112 is angled outwardly such that the outer surface 116 is angled toward an outer portion 111 of the resilient seal 28 at an angle $\alpha$ of approximately 80°.

The lip portion 112 is constructed such that its outer surface 116 will engage an adjacent surface of the inner wall 16 of the sterilizer chamber 14 when the door is in its fully closed position. Further, due to the thin or membrane-like nature of the lip portion 112, pressure from the interior of the chamber 14 will act upon the inner surface 114 of the lip portion 112 to cause the outer surface 116 thereof to be biased into engagement with the inner surface 16 of the chamber 14. Thus, the lip portion 112 provides a seal wherein the outer sealing surface 116 is increasingly biased into engagement with the inner wall 16 of the chamber as the pressure within the chamber 14 increases.

Figure 6:
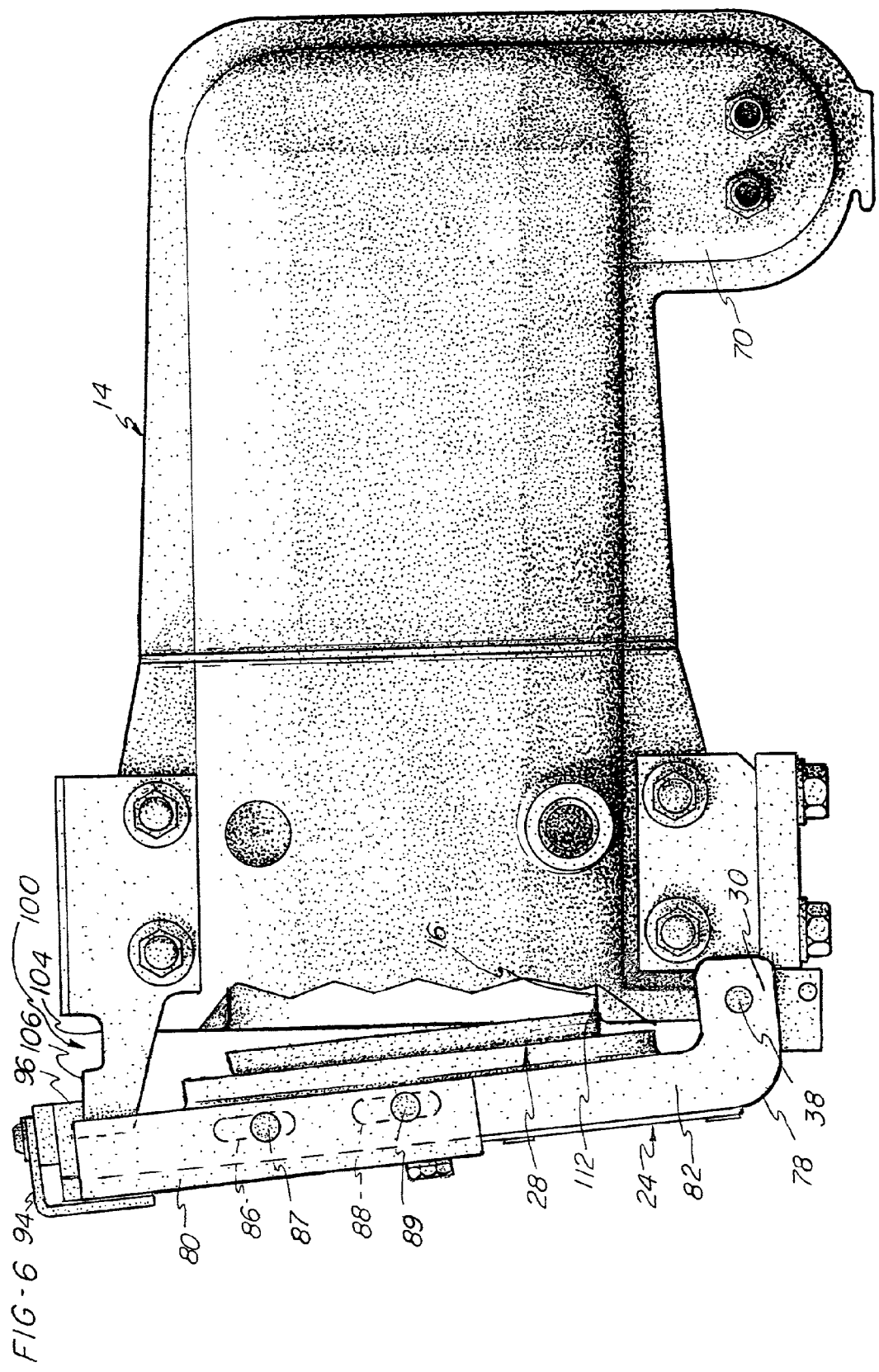
FIG. 6 is a side elevational view of the sterilizer chamber and door showing the door in a partially open position, and with a portion of the chamber cut away to show the seal.

A further function of the lip portion 112, as seen in FIG. 6, is to provide a bridge between the door 24 and the inner wall 16 of the chamber 14 when the door 24 is in its partially open position. The combination of providing a horizontal hinge axis below the chamber 14 and an outwardly extending lip seal structure provides a configuration which bridges the gap between the door 24 and the access opening 20 defined by the front face 18 whereby dripping of condensation from the door 24 and chamber 14 is prevented when the door 24 is in its partially open position for permitting evaporation of moisture and cooling of articles within the chamber 14 subsequent to a sterilization process. Further, the lip portion 112 forms a cup-like configuration on the inner surface of the door 24 such that retained moisture or condensation is retained on the seal 28 as the door 24 is moved to its fully open position (FIG. 2).

Figure 9:
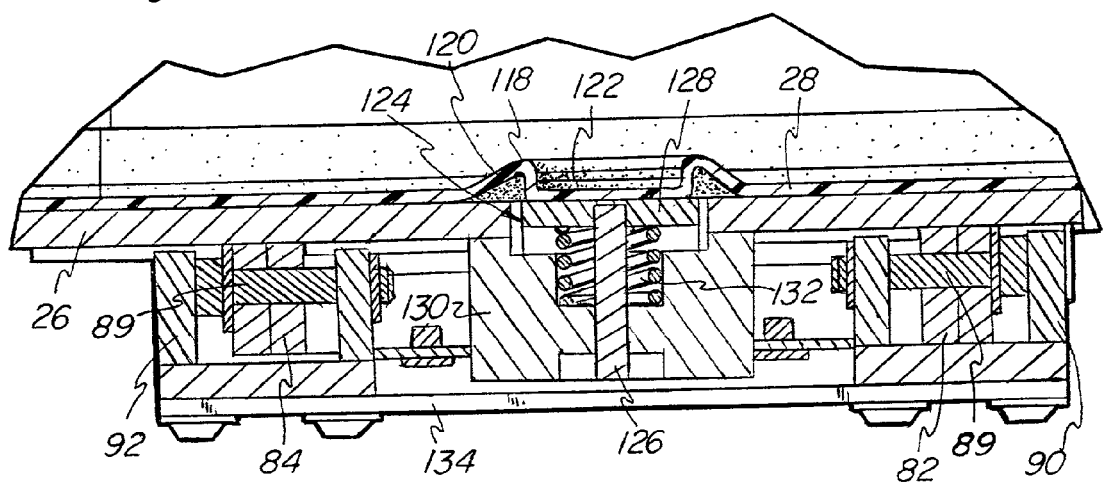
FIG. 9 is a cross-sectional view through the door taken along line 9—9 in FIG. 7 showing the pressure lock mechanism in an unlocked position.

Referring to FIGS. 2, 9 and 10, the resilient seal 28 includes a bellows-structure 118 located centrally on the door 24 including a raised flexible wall portion 120 and a central substantially planar portion 122. The bellows structure forms a cover over a pressure lock 124 located within the sealing plate 26 of the door 24. The pressure lock 124 comprises a plunger weldment including a plunger 126 and an actuator disk 128 rigidly attached to one end of the plunger 126. The pressure lock 124 is supported in a block structure 130 attached to the sealing plate 26, and a coil spring 132 is positioned to bias the actuator disk 128 away from the block 130 and towards the interior of the chamber 14 (FIG. 9).

Figure 7:
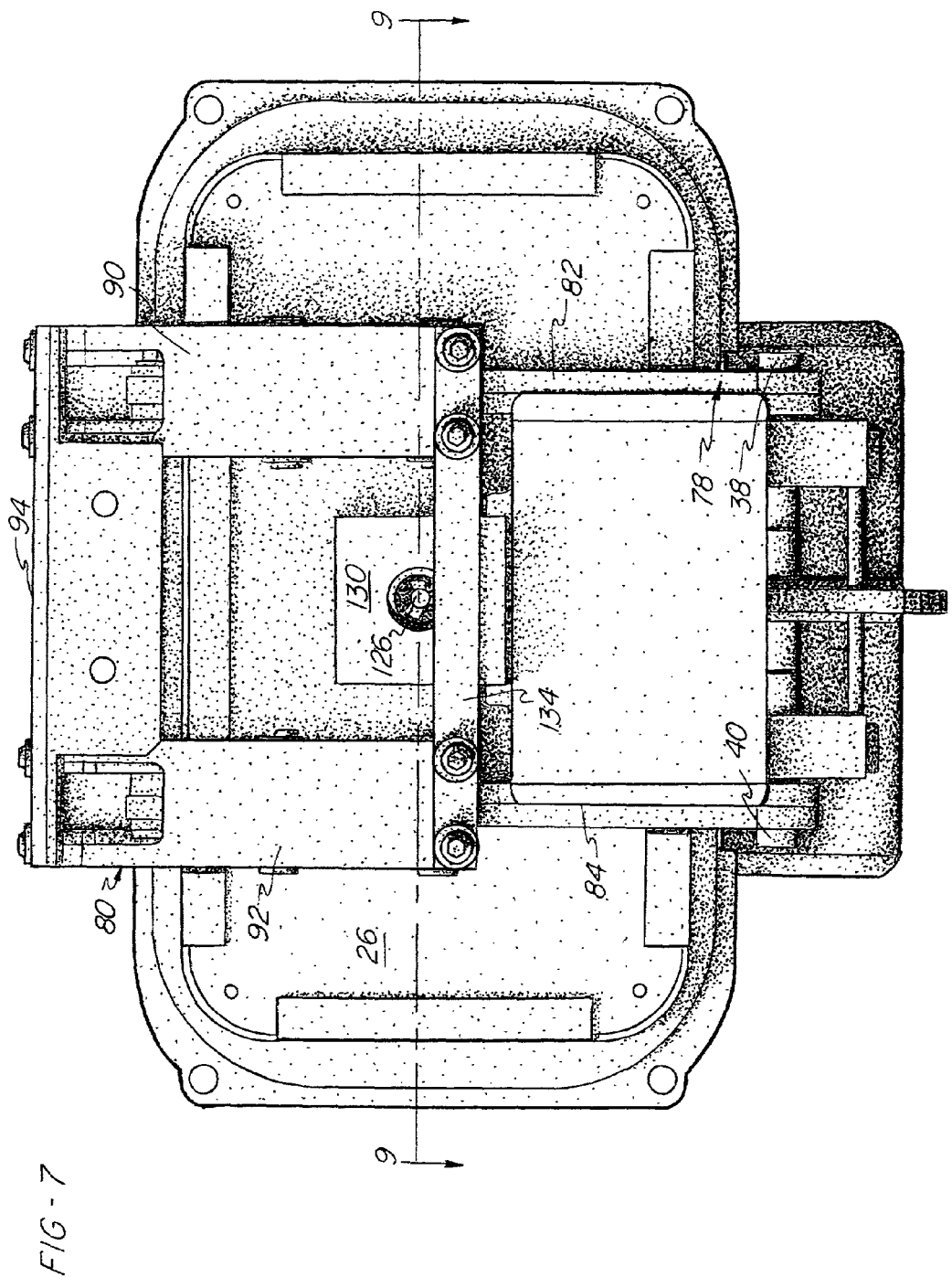
FIG. 7 is a front elevational view of the door showing the latch mechanism in a latched position corresponding to the fully closed position of the door.
Figure 8:
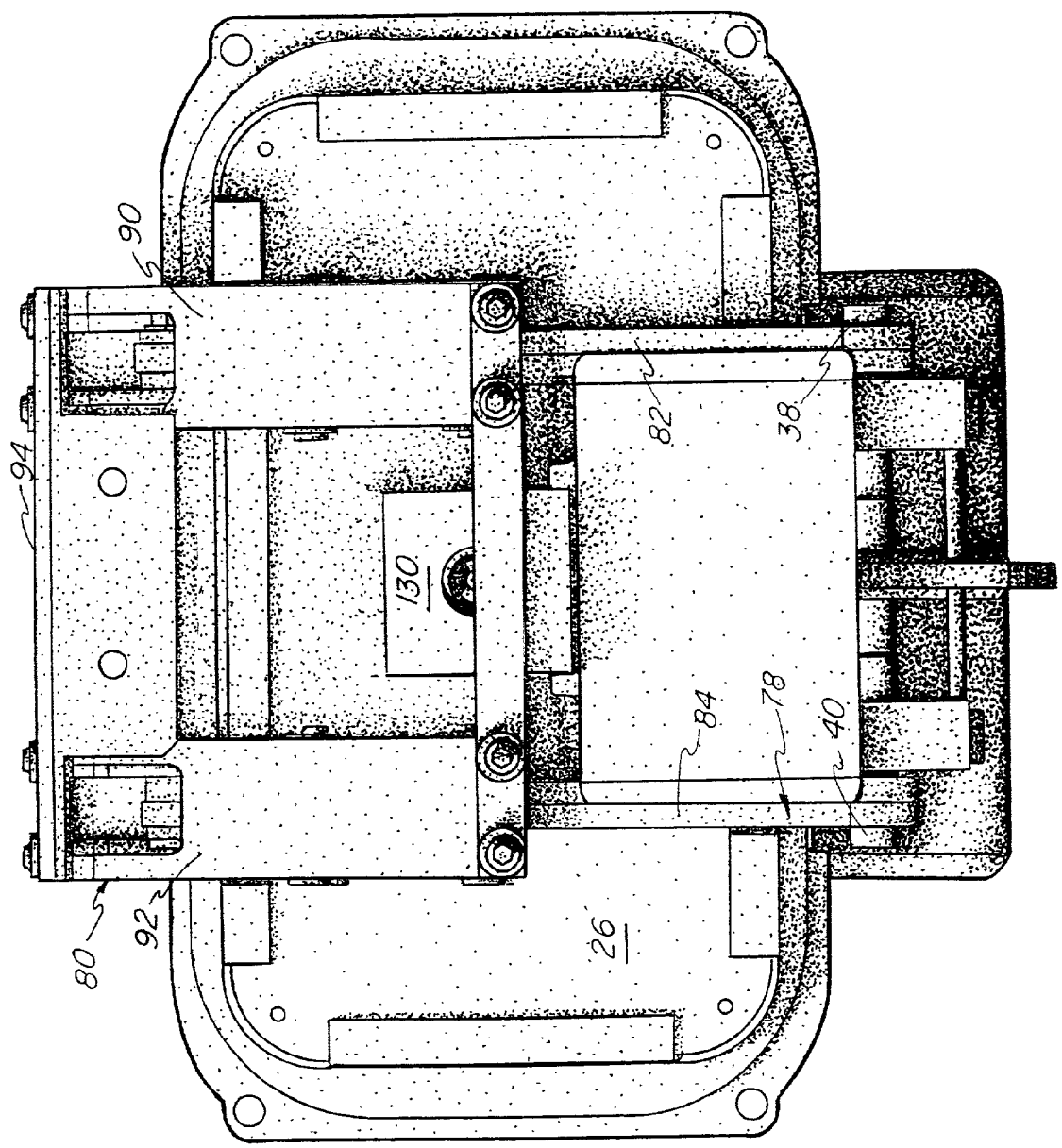
FIG. 8 is a front elevational view of the door showing the latch mechanism in an unlatched position corresponding to a partially open position of the door.

As pressure within the sterilizer chamber 14 increases, it will act upon the actuator disk 128 through the planar portion 122 of the seal 28 to thereby push the disk 128 and plunger 126 outwardly against the biasing force of the spring 132 (FIG. 10). As seen in FIG. 7, a lower horizontal bar 134 extends between the vertical guide members 90, 92 and defines a lock member for preventing upward movement of the sliding frame 80, and resulting disengagement of the latch members 96, 98 from the catch members 100, 102. In particular, as pressure within the chamber 14 increases, the plunger 126 is caused to move outwardly into the path of vertical movement of the lower horizontal bar 134, thereby locking the bar 134 against vertical movement. When the pressure in the chamber 14 decreases to a level where it is safe to open the door 24, the spring 122 will act on the actuator disk 128 to cause the plunger 126 to withdraw away from the bar 134. Accordingly, the lock mechanism 124 provides a simple mechanism for positively locking the door latching mechanism 80 against opening when the sterilizer 10 is pressurized.

Referring to FIGS. 2–4 and 11, the sterilizer 10 is provided with a release mechanism for automatically unlatching the door 24 at the end of the sterilization cycle. The release mechanism includes a pivot rod 136 supported for rotational movement above the chamber 14 at the front portion of the sterilizer 10. A release lever 138 is attached to one end of the rod 136, and an actuation lever 140 is attached to an opposite end thereof. The release lever 138 extends forwardly to a location between the catch members 100, 102 whereby a forward end 142 of the lever 138 is positioned beneath the horizontal bar 94 of the sliding frame 80 when the door 24 is in its fully closed position.

An end of the actuation lever 140 opposite its attachment to the rod 136 is connected to a release mechanism solenoid 144 having a vertically movable plunger 146. Actuation of the solenoid 144 causes the plunger 146 to move downwardly whereby the rod 136 rotates to cause the forward end 142 of the release lever 138 to move upwardly whereby the latch members 96, 98 are disengaged from the first step 104 of the catch members 100, 102 and are positioned in engagement with the second step 106 to permit the door 24 to move to its partially open position (FIG. 6).

In addition, the door 24 is provided with a handle 148 (FIG. 1) connected to the sliding frame 80. The handle 148 may be manually moved upwardly to further disengage the latch members 96, 98 from the second step 106 of the catch members 100, 102 to thereby permit movement of the door 24 to its fully open position.

Figure 12:
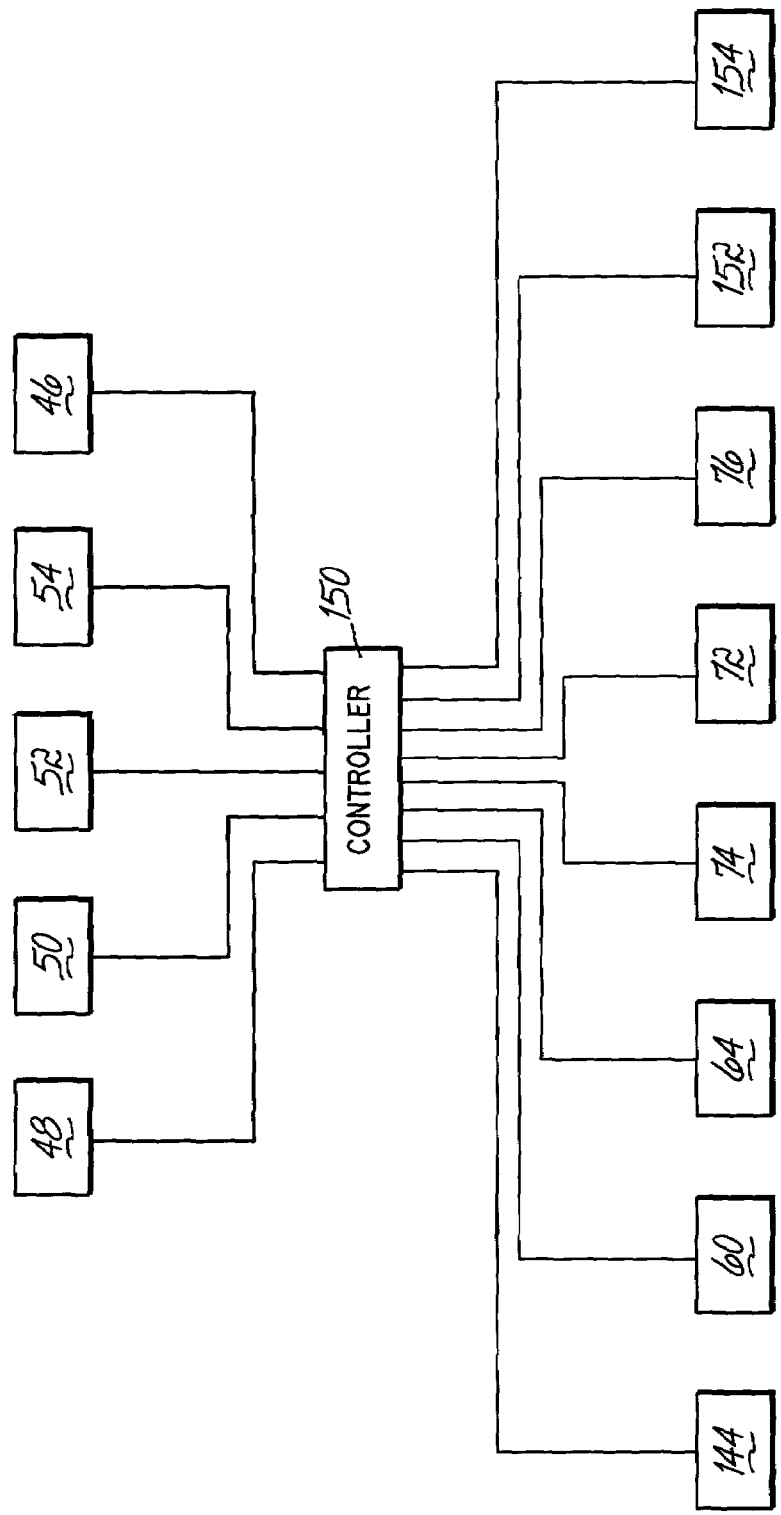
FIG. 12 is a diagrammatic view illustrating the electrical components for controlling operation of the sterilizer.

Referring to FIG. 12, the sterilization cycles of the present sterilizer 10 are controlled by a controller 150 which is connected to the control panel display 46 and buttons 48, 50, 52, 54. In addition, the controller controls the operation of the solenoids 60, 64, 74 controlling flow of air, water and steam to and from the chamber 14, and further controls the heaters 72, 76 and the release mechanism solenoid 144. Also, the controller 150 receives inputs from sensors located in the chamber 14 for measuring gas properties within the chamber 14, including temperature sensors 152 and a pressure sensor 154 for measuring the chamber temperature and pressure.

As mentioned previously, an operator may select different cycles for sterilizing articles within the sterilizer chamber 14, including unwrapped articles, as selected by button 48, and wrapped articles, as selected by button 50. In accordance with a method of using the sterilizer, articles are placed within the sterilizer chamber 14, and steam is supplied to the chamber 14 by opening solenoid valve 64 to permit water to enter the chamber 14, and the heater 72 is energized to heat the water in the basin portion 70 and to heat the chamber walls. As water enters the chamber 14, the chamber conditions are substantially atmospheric and the controller captures and stores the absolute (barometric) pressure from pressure sensor 154. This barometric pressure measurement is used by the controller for subsequent steam quality calculations. The controller also calculates a pre-boiling temperature for the water in the chamber based on the measured barometric pressure. In this manner, the sterilizer is able to adjust operation to account for changes in altitude which may affect the temperature at which steam is formed within the chamber.

Purge valve 60 is left open while the water is heated to boiling to permit air which has been trapped in the chamber 14 to exit as the air expands due to heating and is displaced by water vapor. When the controller 150 senses that the temperature in the chamber 14 has reached the calculated pre-boiling temperature, purge valve 60 is closed to permit pressure within chamber 14 to increase. As steam continues to form within the chamber 14, the controller 150 monitors the gas properties as sensed by the sensors 152, 154, and at least one of the gas properties (i.e., temperature and pressure) is compared by the controller 150 to a predetermined value for that gas property. Upon the monitored gas property reaching a predetermined value, the purge valve 60 may be opened for a predetermined period of time, whereby the percentage of air relative to steam in the chamber 14 is decreased During this portion of the cycle, as the pressure within the chamber 14 is increasing, the lock mechanism 124 is automatically actuated by the pressure to thereby lock the door 24 against opening.

In the preferred embodiment, the controller 150 is programmed with temperature and pressure values corresponding to saturated steam conditions. The controller 150 continues to monitor the temperature and pressure during heat-up and formation of steam and is programmed to open the purge valve 60 in response to conditions within the chamber deviating a predetermined amount from saturated steam conditions, such that the purge valve 60 may be opened a plurality of times at various intervals to purge as much air as possible from the chamber 14 prior to beginning the Sterilization Mode of the cycle. The controller 150 also monitors chamber conditions and operates purge valve 60 during Sterilization Mode, to ensure that chamber conditions approach saturated steam conditions as closely as possible.

Figure 13:
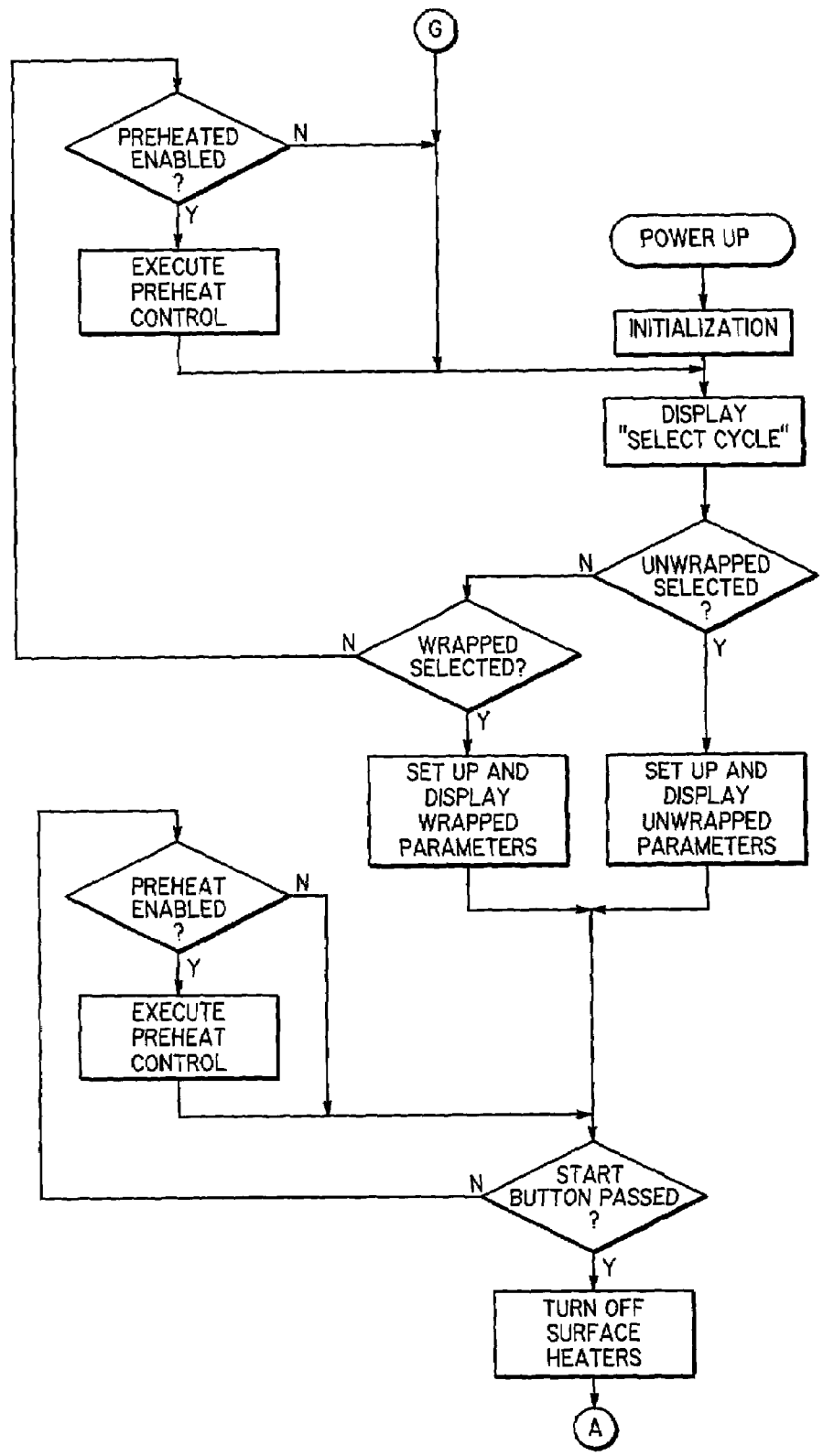
FIG. 13 is a flow chart depicting the operation of the sterilizer during a cycle selection mode of the sterilization process.

Referring to FIGS. 13 thru 21, the operation of the controller 150 will be described with reference to the steps performed during a sterilization cycle. Referring initially to FIG. 13, during a cycle selection mode of the sterilization process, the controller 150 initially monitors the buttons 48, 50 after power up of the sterilizer, to determine the type of cycle, wrapped or unwrapped, selected from the control panel 44. Once the type of cycle is selected, the controller 150 then monitors the start button 52 which must be depressed before the sterilization process will proceed further. During this mode of operation, the sterilizer chamber 14 is preferably undergoing a preheat operation preformed in accordance with the processes described with regard to FIG. 20 below, and in which the auxiliary heater 76 and steam heater 72 are cycled according to a proportional duty scheme to maintain the chamber 14 in a heated condition.

Figure 14:
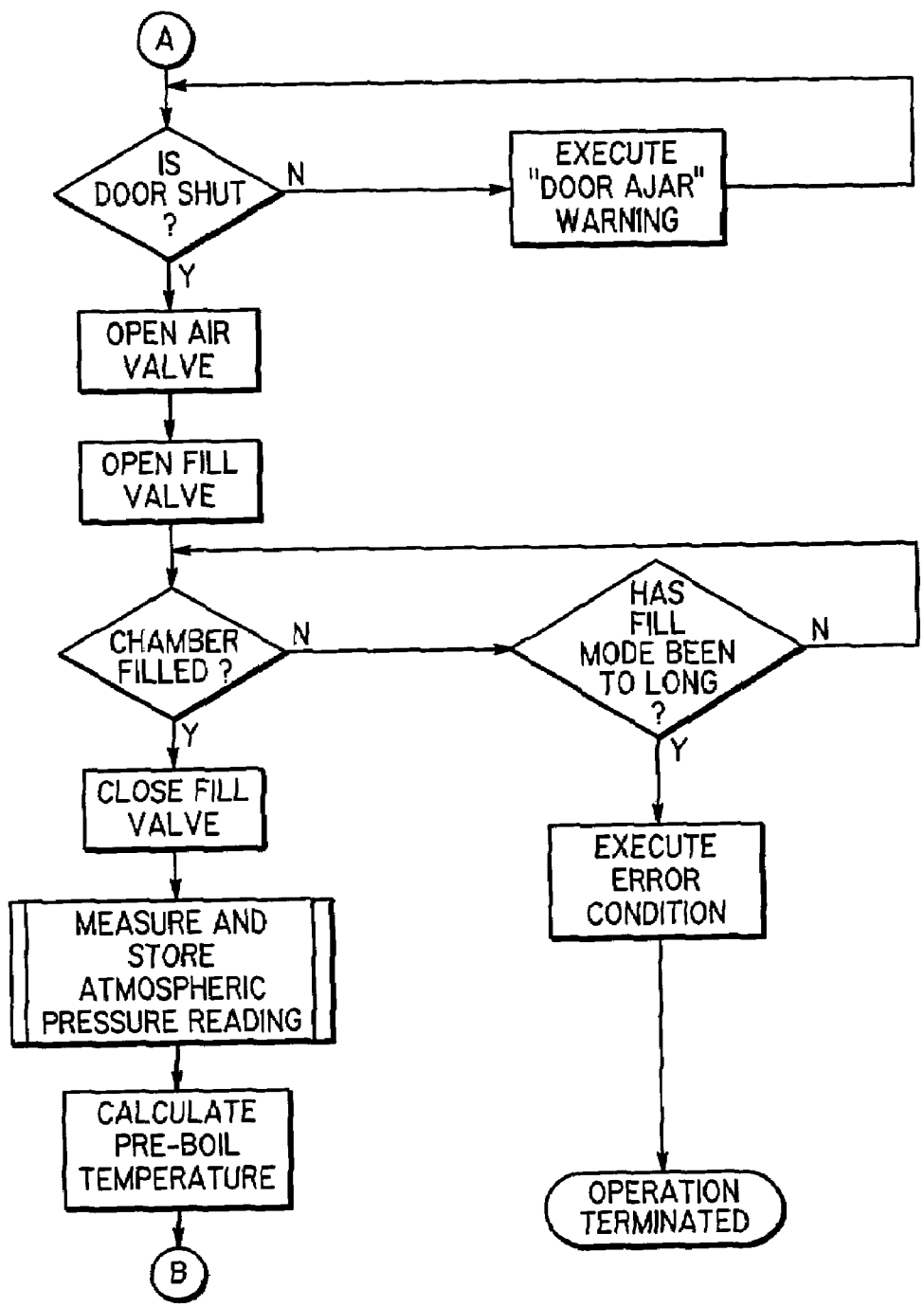
FIG. 14 is a flow chart depicting the operation of the sterilizer during a Fill Mode of the sterilization process.

Referring further to FIG. 14, when the start button 52 is depressed, auxiliary heater 76 and steam heater 72 are turned off and the sterilizer begins a Fill Mode of operation. Initially, the controller 150 monitors the door to insure that it is shut and, upon sensing that the door is shut, opens the air or purge valve 60 and opens the fill valve 64 to permit water to flow into the chamber 14. After the chamber is filled, the fill valve 64 is closed and the controller 150 measures and stores the barometric pressure as a reference pressure and calculates the pre-boil temperature.

Figure 16:
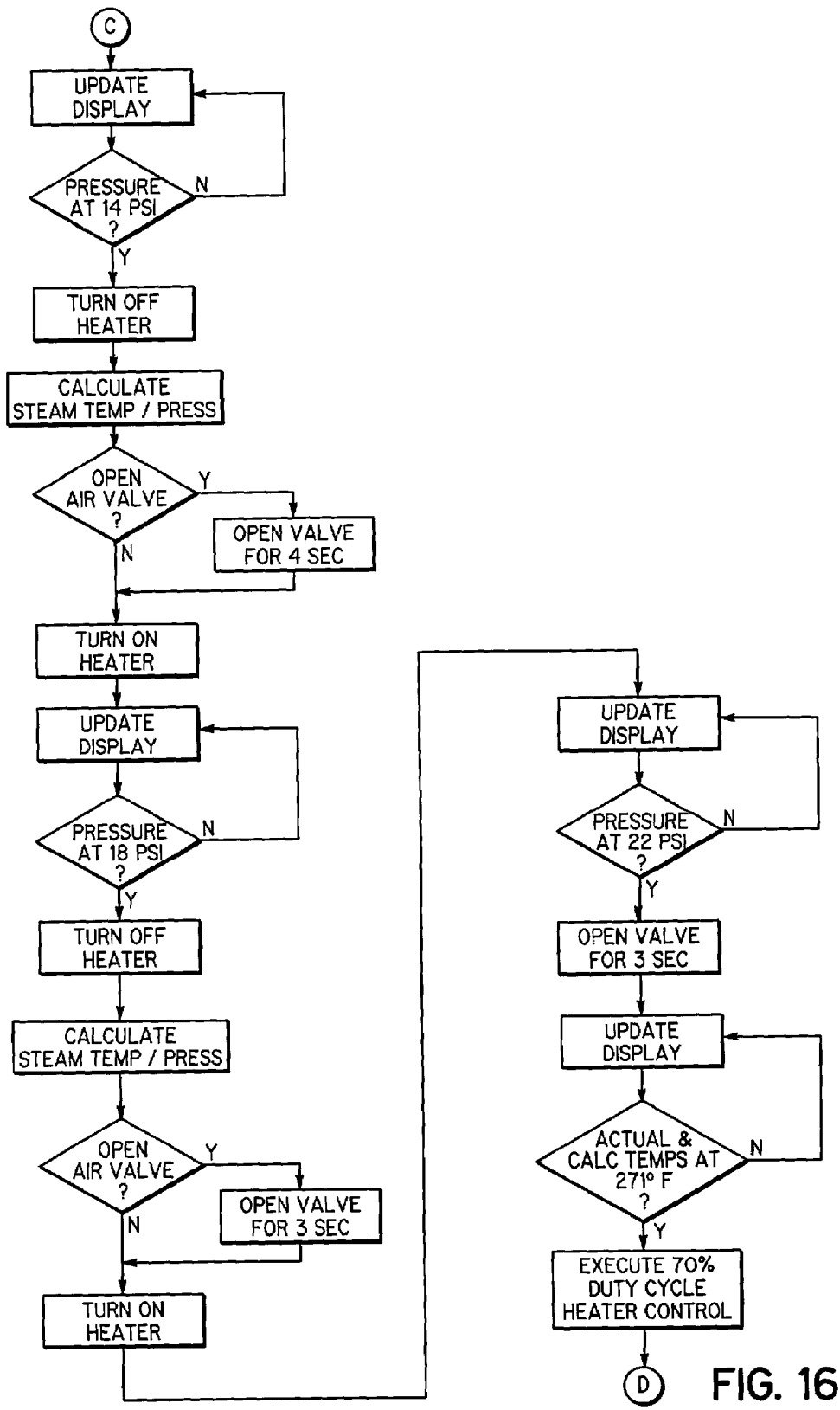

Referring to FIGS. 15–16, the sterilization process continues with a Heat-up Mode of operation when the heater element 72 is energized to heat the water within the chamber 14 and form steam. The controller 150 monitors the temperature during heat-up, and when the temperature reaches the calculated pre-boil temperature, the purge valve 60 is closed to allow pressure within chamber 14 to increase. When the pressure within chamber 14 reaches 6 psi (41.4 kPa), the purge valve 60 is opened for 6 seconds to permit the release of air which has been displaced by steam within the chamber 14, then purge valve 60 is closed again. While some steam may inevitably escape during this and subsequent air purges, there is more than enough water provided during the Fill Mode which may be converted to steam to replace the loss.

At intervals corresponding to the pressure inside chamber 14 reaching 10 psi (68.9 kPa), 14 psi (96.5 kPa), and 18 psi (124.1 kPa), the controller 150 samples the pressure and temperature conditions within the chamber 14 and compares them to the preprogrammed values for saturated steam. If the difference between the preprogrammed value for pressure at the measured temperature and the pressure sensed by pressure sensor 154 is more than 1.45 psi (10 kPa), purge valve 60 is opened for 3 to 5 seconds to purge air from the chamber 14. To account for any difference in response time that may exist between pressure sensor 154 and temperature sensor 152, the steam heater 72 is turned off until the measured pressure and temperature begin to decrease (generally 3 to 5 seconds). The measured local maximum values of temperature and pressure are captured by the controller 150 and then used by the controller 150 to perform the calculations. After the local maximum temperature and pressure values have been captured, heater 72 is turned back on again.

Finally, when the pressure in chamber 14 reaches 22 psi (151.7 kPa) purge valve 60 is opened for 3 seconds, regardless of the temperature and pressure conditions inside the chamber 14. By purging air in this manner, the conditions inside the chamber are urged toward saturated steam conditions such that approximately 0.35% or less retained air is present within the chamber 14. These conditions provide more accurate measurements of pressure and temperature within the chamber 14 to ensure that sterilization of articles placed in the chamber 14 meets sterilization standards.

When the temperature within the sterilizer chamber 14 reaches approximately 271° F. (132.8° C.), the sterilizer begins a Sterilization Mode in accordance with the selected sterilization process for either wrapped or unwrapped articles. As seen in FIG. 17, the controller 150 sets a count-down timer, and the heater 72 is cycled on and off according to a proportional duty cycle scheme to maintain the temperature in chamber 14 at a desired sterilization set point. Specifically, if the temperature within the chamber 14 is greater than or equal to 272.4° F. (133.6° C.) the heater 72 is controlled to permit the temperature within the sterilizer chamber to fall. Alternatively, if the temperature within the chamber 14 is less than or equal to 272° F. (133.3° C.) the heater 72 is controlled to cause a temperature rise within the chamber 14.

The heater 72 is controlled according to a predetermined proportional duty cycle scheme, wherein the heater 72 is cycled on and off for varying periods of time, depending on the difference between the measured temperature and a desired temperature to bring the temperature back to the set point temperature, as opposed to fully energizing or de-energizing the heater 76. Specifically, the heater 72 is cycled on for a percentage of a time interval equal to 1 second. If the measured temperature deviates in a direction less than the set point temperature, the heater 72 is cycled on for a greater percentage of the time interval, up to 100%. If the measured temperature deviates in a direction greater than the set point temperature, the heater 72 is cycled on a smaller percentage of the time interval, and approaches a condition of remaining off during the entire time interval. Prior to entering Sterilization Mode, heater 72 is cycled at 70% duty cycle (i.e. the heater is on during 70% of the time interval) as shown in FIG. 16, to reduce temperature overshoot which may occur when first entering Sterilization Mode.

During Sterilization Mode, controller 150 monitors the pressure and temperature within the chamber 14 and performs a comparison of measured steam conditions to saturated steam conditions similar to that described above for the Heat-up Mode. If the measured value of pressure differs from the preprogrammed value of pressure at the measured temperature by more than 0.44 psi (3 kPa) then purge valve 60 is opened for 0.25 seconds to "burp" excess air from the chamber 14. The controller 150 will permit the purge valve 60 to burp air only in 30 second intervals, beginning 30 seconds after Sterilization Mode has begun.

In addition to monitoring pressure and temperature to determine if air in the chamber 14 needs to be expelled, controller 150 compares the measured values of pressure and temperature to maximum and minimum limits which correspond to sterilization conditions specified in standard AAMI-ST55, established by the Association for the Advancement of Medical Instrumentation. Specifically, if the measured temperature exceeds 275.3° F. (135.2° C.) or falls below 270.7° F. (132.6° C.), or if the measured pressure exceeds 45.9 psi (316.6 kPa) (absolute) or falls below 42.2 psi (290.7 kPa) (absolute); or if the measured pressure exceeds the preprogrammed pressure at the measured temperature by more than 1.6 psi (11.0 kPa), then the sterilization cycle is aborted and the sterilizer cycles through another Fill Mode and Heat-up Mode, and begins a new sterilization cycle without the need for user intervention.

Figure 18:
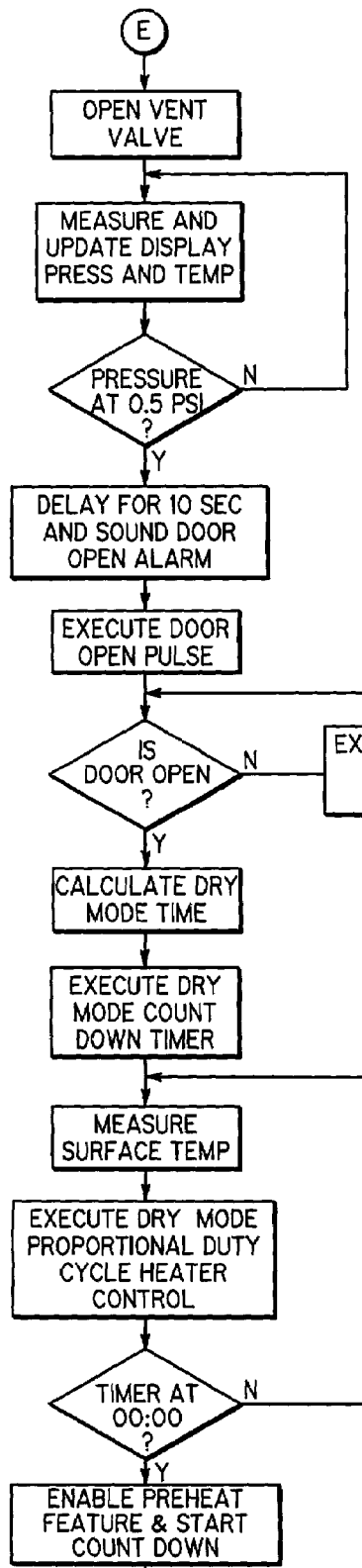
FIGS. 18 and 19 are flow charts depicting the operation of the sterilizer during a vent and process completion mode of the sterilizer.

If the sterilizer progresses through Sterilization Mode without exceeding the maximum and minimum limits and the countdown timer reaches zero, the heater 72 is turned off and the sterilizer enters a Vent and Dry Mode, as illustrated in FIG. 18. Specifically, the solenoid valve 74 is opened to vent steam from the chamber 14 and when the pressure within the chamber reaches 0.5 psi (3.4 kPa), the release mechanism solenoid 144 is actuated after a 10 second dely to lift the latch mechanism 80. The residual pressure within the chamber 14 pushes the door 24 out to its partially open position to permit cooling and moisture evaporation from the articles.

The duration of the Dry Mode is variable and depends on the steam temperature attained between Fill Mode and Heat-up Mode. This duration is determined from the equation:

$$y = mx + b$$

where: y=the drying time in seconds
m=−20.41 seconds/° C.
x=Heat-up Mode initial temperature (° C.)
b=2967.77 seconds Regardless of the dry time calculated, the Dry Mode duration is bounded by a minimum of 20 minutes and a maximum of 40 minutes, to provide a short sterilization time while preventing the scorching of towels used to wrap articles placed within the sterilizer. During the Dry Mode, auxiliary heater 76 and steam heater 72 are cycled according to a proportional duty cycle scheme as was described for the Sterilization Mode. The Dry Mode, however, incorporates a duty cycle scheme having three different set point temperatures based on the total drying time, wherein the set point temperature is 545.0° F. (285.0° C.) for the first 17.5% of the drying time, 428.0° F. (220.0° C.) for the second 17.5% of the drying time, and 320.0° F. (160.0° C.) for the final 65.0% of the drying time.

Figure 20:
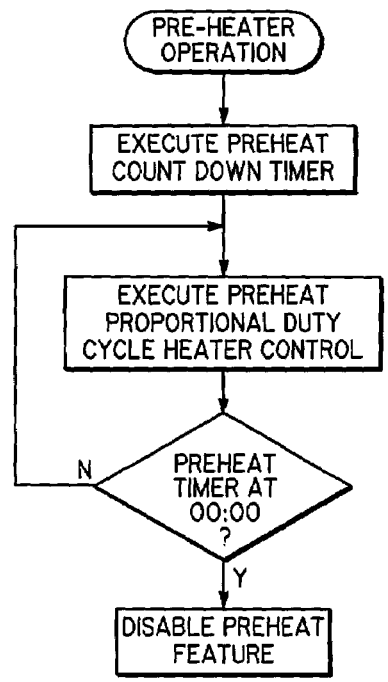
FIG. 20 is a flow chart depicting the operation of the sterilizer during a Pre-heat Mode of the sterilization process.
Figure 21:
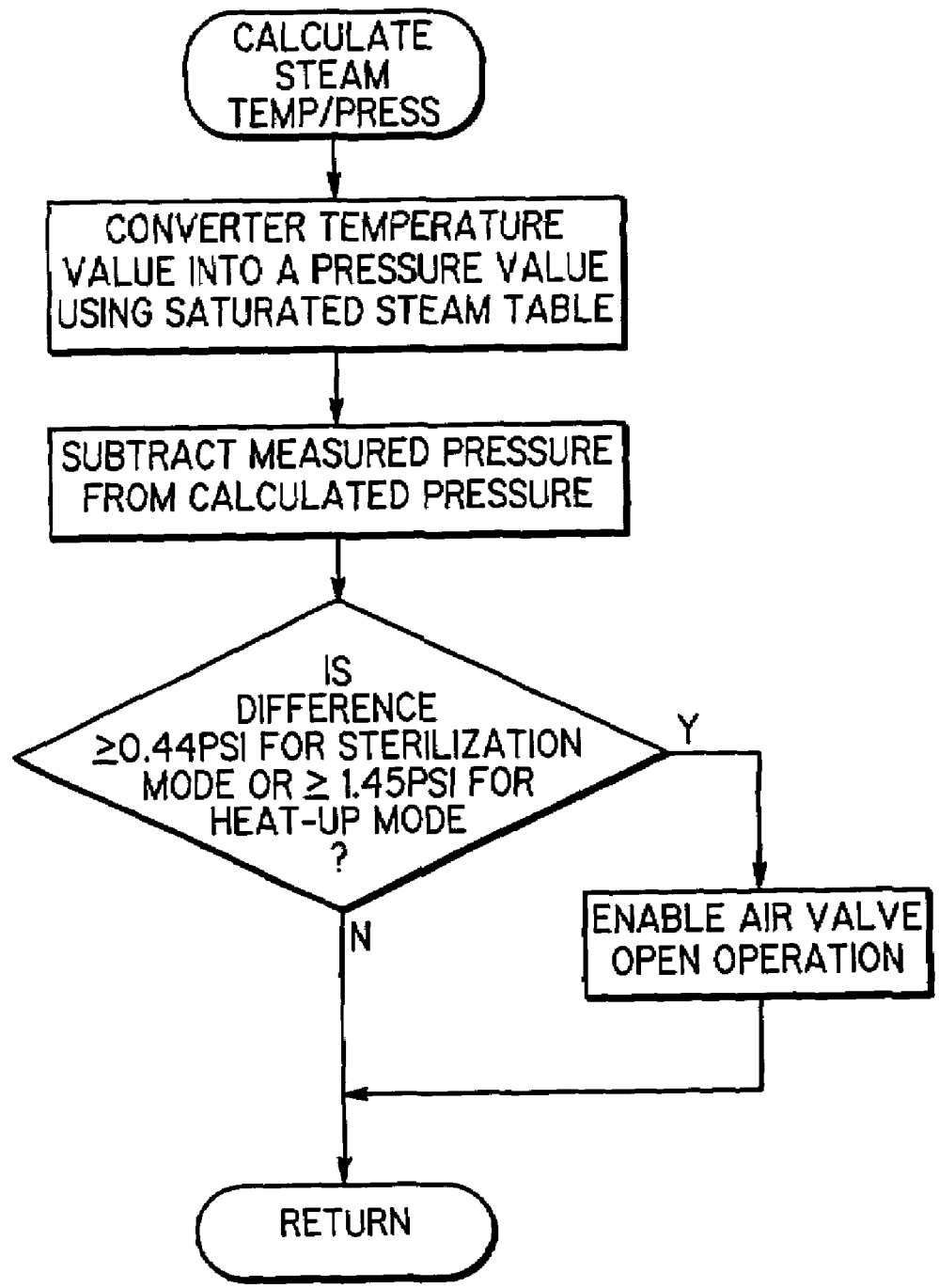
FIG. 21 is a flow chart depicting a sub routine of the sterilizer for determining and adjusting the conditions within the sterilizer chamber during the Heat-up Mode of the sterilization process.

At the end of the Dry Mode of the sterilization process, a preheat operation in enabled, as illustrated in the flow chart of FIG. 20, to maintain the surface temperature of the sterilizer at a set point of 248° F. (120° C.) for a predetermined period of time, such as for one hour, as determined by a preheat timer, so that the sterilizer is in a preheated condition and ready for a further sterilization process. During pre-heat, auxiliary heater 76 and steam heater 72 are cycled on and off according to a proportional duty scheme to maintain the desired temperature. The proportional duty scheme is similar to that described above for Sterilization Mode, but is bounded by a maximum of 50% duty cycle.

Figure 19:
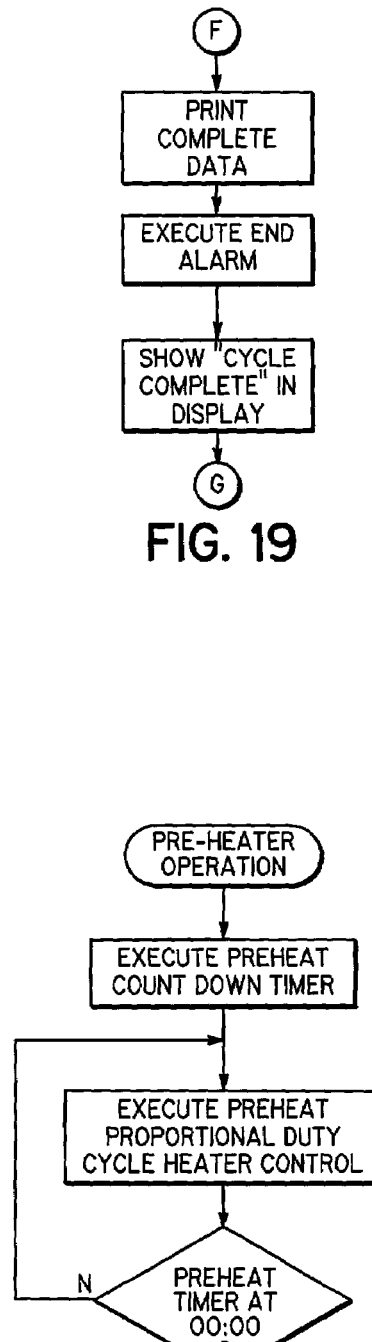

Referring to FIG. 19, the sterilization process is concluded by printing data relating to the sterilization process, executing an alarm to alert an operator to the end of the sterilization process and providing a message on the display 46 advising that the sterilization cycle is complete. It should be noted that the printing operation may be performed by a printer mounted to the sterilizer at 160.

From the above description, it should be apparent that the present sterilizer provides an improved system for sterilizing articles, including an improved access opening incorporating a seal which facilitates retention of condensation in the sterilizer during a cool down mode of a sterilization cycle, as well as providing an improved seal between the sterilizer door and the chamber. Further, the present sterilizer provides an improved steam generation mode for a sterilization cycle wherein a greater percentage of steam relative to residual air is provided to ensure proper sterilization of articles.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A sterilizer for providing a heated and pressurized steam environment for sterilizing articles, said sterilizer comprising:
   a sterilizing chamber for receiving articles to be sterilized, said chamber including an inner wall defining a chamber interior;
   a planar surface defining a front face formed generally perpendicular to and excluding outwardly from said inner wall, said front face defining a chamber opening for access to said chamber interior;
   a door mounted for movement relative to said chamber between a fully closed position wherein said door is in engagement with said front face and a fully open position wherein an operator may access the chamber interior for insertion and removal of articles therein; and
   a resilient seal between said door and said chamber interior, said seal comprising an annular lip having opposing inner and outer surfaces, said lip extending from said door into said chamber with said outer surface of said lip in engagement with said inner wall of said chamber whereby pressure within said chamber acts on said inner surface of said lip to bias said outer surface of said lip into engagement with said inner wall of said chamber.

2. The sterilizer of claim 1 including a mechanism for latching said door in a partially open position spaced from said chamber opening and intermediate said fully closed position and said fully open position wherein, in said partially open position, said lip forms a bridge extending between said inner wall and said door whereby said lip inhibits dripping of condensation from said door and said chamber.

3. The sterilizer of claim 2 wherein said door is supported for movement about a horizontal pivot axis extending adjacent a bottom edge of said chamber opening.

4. The sterilizer of claim 1 wherein said door includes a pressure lock having an actuator mechanism actuated by pressure in said chamber to lock said door in said fully closed position, and said resilient seal extends inwardly from said lip over an inner surface of said door to provide a flexible cover for said actuator mechanism.

5. The sterilizer of claim 4 including a latching mechanism for latching said door in said fully closed position, said latching mechanism including a moveable latch located on said door and a catch located in stationary relationship to said chamber, said latch engaging said catch to prevent movement of said door, said latching mechanism further including a lock member connected to said latch for movement with said latch, and said pressure lock including a plunger moveable into the path of said lock member to prevent movement of said lock member and said latch when a predetermined pressure is present within said chamber.

6. A sterilizer for providing a heated and pressurized steam environment for sterilizing articles, said sterilizer comprising:
   a sterilizing chamber for receiving articles to be sterilized, said chamber including an inner wall defining a chamber interior;
   a planar surface defining a front face formed generally perpendicular to and extending outwardly from said inner wall, said front face defining a chamber opening for access to said chamber interior;
   a door supported for movement about a horizontal axis relative to said chamber between a fully closed position wherein said door is in engagement with said front face and a fully open position wherein an operator may access the chamber interior for insertion and removal of articles there;
   a mechanism for latching said door in an intermediate position between said fully open position and said fully closed position; and
   a resilient seal between said door and said chamber interior wherein, in at least the intermediate position of said door between said fully open position and said fully closed position, said resilient seal extends from said door into said chamber interior across a lower edge of said chamber whereby said resilient seal inhibits dripping of condensation from said door and said chamber.

7. The sterilizer of claim 6 wherein said resilient seal is attached to said door and includes a lip extending transverse to an inner surface of said door.

8. The sterilizer of claim 7 wherein, in said fully closed position of said door, said lip extends inside said chamber and into contact with said inner wall whereby increasing pressure within said chamber interior biases said lip into sealing engagement with said inner wall.

9. The sterilizer of claim 6, wherein said latching mechanism includes a moveable latch located on said door and a catch to prevent movement of said door, said latching mechanism further including a lock member connected to said latch for movement with said latch, and including a pressure lock comprising a plunger moveable into the path of said lock member to prevent movement of said lock member and said latch when a predetermined pressure is present within said chamber.

10. The sterilizer of claim 9 wherein said plunger is actuated by an actuator mechanism extending through said door, and said resilient seal extends over an inner surface of said door and forms a flexible cover over said actuator mechanism whereby said actuator mechanism is actuated by pressure within said chamber.

11. A sterilizer for providing a heated and pressurized steam environment for sterilizing articles, said sterilizer comprising:
    a sterilizer chamber for receiving articles to be sterilized, said chamber including an inner wall defining a chamber interior and means defining a chamber opening;
    a door mounted for movement relative to said chamber between a fully closed position wherein said door is in sealing engagement over said chamber opening and a fully open position wherein an operator may access the chamber interior for insertion and removal of articles therein;
    a heater and water source providing steam to said chamber interior;
    control means for monitoring and controlling a sterilization process;
    temperature and pressure sensing means connected to said control means for sensing temperature and pressure, respectively, within said chamber interior; and
    a purge valve in fluid communication with said chamber interior, said control means opening said purge valve to purge air from said chamber interior in response to at least one of said temperature and pressure sensor means sensing a predetermined condition within said chamber during formation of steam within said chamber whereby the percentage of air relative to steam within said chamber is decreased.

12. The sterilizer of claim 11 wherein said control means opens said purge valve in response to input from said temperature and pressure sending means indicating a deviation from a saturated steam condition within said chamber.

13. The sterilizer of claim 11 including a seal between said door and said chamber opening wherein said seal includes a lip supported for engagement with said inner wall and located such that pressure within said chamber interior will force said lip into sealing engagement with said inner wall.

14. The sterilizer of claim 13 including a mechanism for latching said door in a partially open position spaced from said chamber opening and intermediate said fully closed position and said fully open position wherein, in said partially open position, said lip forms a bridge extending between said inner wall and said door whereby said lip inhibits dripping of condensation from said door and said chamber.

15. The sterilizer of claim 14 including a solenoid connected to a release mechanism for unlatching said door and connected to said control means wherein said control means actuates said solenoid in response to a sensed pressure in said chamber decreasing to a predetermined value after a sterilization process whereby said mechanism for latching said door is released to permit said door to move to said partially open position.

16. The sterilizer of claim 11 including a seal supported on said door for forming a pressure seal between said door and said chamber opening wherein said door includes a pressure lock actuated by pressure in said chamber to lock said door in said fully closed position, and said seal extends inwardly from said lip over an inner surface of said door to provide a flexible cover for an actuator mechanism for said pressure lock.

17. A method of sterilizing articles in a sterilizer including a sterilizing chamber defining a chamber interior for containing articles to be sterilized and a door for closing said chamber, said method comprising the steps of:
    placing articles to be sterilized within said chamber;
    supplying said chamber with steam;
    monitoring gas properties within said chamber, said gas properties comprising temperature and pressure;
    comparing said gas properties to predetermined values for said gas properties; and
    automatically opening a purge valve of said chamber in response to said gas properties reaching said predetermined values whereby air is released from said chamber to decrease the percentage of air relative to steam in said chamber.

18. The method of claim 17 wherein said step of comparing comprises comparing the temperature and pressure within said chamber to a predetermined saturated steam condition, and said step of opening said purge valve comprises opening said purge valve if the temperature and pressure within said chamber deviates from said predetermined saturated steam condition.

19. The method of claim 17 wherein said step of opening said purge valve comprises opening said purge value for a preset period of time.

20. The method of claim 17 wherein said step of opening said purge valve comprises opening said purge valve a plurality of times, each opening of said purge valve corresponding to at least one of said gas properties within said chamber reaching a predetermined value to thereby cause said comparison step to be performed.

21. The method of claim 17 including the step of holding the temperature within said chamber near a predetermined maximum value for a predetermined period of time after a saturated steam condition is reached within said chamber whereby articles within said chamber are sterilized.

22. The method of claim 17 including the step of causing a lock to be actuated in response to an increased pressure within said chamber to thereby lock said door closed.

23. The method of claim 17 wherein the sterilizer includes a seal located between said door and said chamber interior, the method further including the step of:
    biasing said seal into sealing engagement between said door and said chamber interior in response to increased pressure within said chamber interior.

24. The method of claim 17 including the step of said control means automatically actuating said door to move to a partially open position in response to a sensed pressure in said chamber decreasing to a predetermined value following a sterilization operation.

25. A method of sterilizing articles in a sterilizer having a sterilizing chamber, pressure and temperature sensors for measuring pressure and temperature in said chamber, and a controller including a table of corresponding pressures and temperatures, comprising:
    measuring temperature and pressure in said chamber;
    comparing the measured pressure in said chamber to the pressure in said table corresponding to the measured temperature; and
    altering said measured pressure if it varies by a predetermined amount from the pressure in said table corresponding to the measured temperature until the measured pressure in said chamber is substantially equal to the pressure in said table corresponding to said measured temperature.

26. The method of claim 25 wherein the step of altering the pressure conditions within the chamber includes purging air from the chamber.

27. The method of claim 25 wherein at least some of the predetermined values of pressure and temperature correspond to saturated steam conditions.

28. The method of claim 25 further including the steps of:
periodically comparing measured pressures and temperatures to predetermined values of pressure and temperature corresponding to maximum and minimum limits; and
automatically restarting a sterilization cycle when the measured pressure or temperature values exceed the predetermined pressure and temperature limits.

29. The method of claim 25 wherein the sterilizer further includes a heater for adding heat to the chamber, the method further including the steps of:
controlling the temperature inside the chamber by cycling the heater on and off according to a predetermined schedule based on the difference in measured temperature and a predetermined temperature.

30. The method of claim 29 wherein the measured pressure and temperature are determined during a period when the heater is not on.

31. A method for sterilizing articles in a sterilizer having a sterilizing chamber, a controller including a memory device containing predetermined values of pressure and temperature, a reservoir for supplying a predetermined quantity of water to the chamber, and a vent for venting air in the chamber, the method including the steps of:
placing articles to be sterilized in the chamber;
opening the vent;
filling the chamber with water from the reservoir;
measuring atmospheric pressure;
calculating a temperature at which the water will boil;
heating the water to produce steam;
closing the vent to build pressure when the measured temperature is substantially equal to the calculated boiling temperature;
periodically measuring temperatures and pressures within the chamber;
periodically comparing measured pressures to the predetermined values of pressure at measured temperatures; and
purging air from the chamber if a measured pressure differs from the predetermined pressure by a predetermined amount.

32. The method of claim 31 wherein at least some of the predetermined values correspond to saturated steam conditions and the step of purging air from the chamber occurs when measured pressure differs from the saturated steam pressure by a predetermined amount.

33. The method of claim 32 wherein at least some of the predetermined values correspond to maximum and minimum limits of pressure and temperature, the method further including the steps of;
periodically comparing measured pressures and temperatures to predetermined values of pressure and temperature corresponding to maximum and minimum limits; and
automatically restarting a sterilization cycle when the measured pressure or temperature values exceed the predetermined pressure and temperature limits.

34. The method of claim 32 wherein step of purging air from the chamber when a measured pressure differs from the saturated steam pressure by a predetermined amount continues throughout the sterilization cycle.

35. The method of claim 34 wherein air is purged from the chamber during the sterilization cycle when the measured pressure differs from the saturated steam pressure by an amount equal to or greater than about 3 kPa.

36. The method of claim 32 wherein air is purged from the chamber when the pressure difference is greater than or equal to about 10 kPa and the measured temperature in the chamber is less than about 132.8 C., and air is purged from the chamber when the pressure difference is greater than or equal to about 3 kPa and the measured temperature in the chamber is greater than or equal to about 132.8 C.

37. The method of claim 31 further including the steps of:
opening a valve to release substantially all of the steam from the chamber; and
controlling the temperature inside the chamber to help dry the articles by cycling the heater on and off according to a predetermined schedule based on the difference in measured temperature and a predetermined temperature.

* * * * *

UNITED STATES PATENT AND TRADEMARK OFFICE
CERTIFICATE OF CORRECTION

PATENT NO. : 6,984,359 B2
DATED : January 10, 2006
INVENTOR(S) : Florkey et al.

It is certified that error appears in the above-identified patent and that said Letters Patent is hereby corrected as shown below:

<u>Column 5,</u>
Lines 45-46, reads "The cooperation between...maintain the sliding…" should read
-- The cooperation between…maintains the sliding… --.

<u>Column 8,</u>
Line 14, reads "…chamber 14 is decreased During this portion…" should read
-- chamber 14 is decreased. During this portion… --.
Lines 43-44, reads "…undergoing a heat operation preformed in accordance with the processes described with regard to…" should read -- …undergoing a heat operation performed in accordance with the processes described with regard to… --.

<u>Column 11,</u>
Line 37, reads "…spirit of applicant's general inventive concept." should read
-- …spirit of applicants' general inventive concept. --.
Line 47, reads "…perpendicular to and excluding outwardly from…" should read
-- …perpendicular to and extending outwardly from… --.

<u>Column 12,</u>
Line 41, reads "…insertion and removal of articles there;…" should read -- …insertion and removal of articles therein;… --.

<u>Column 13,</u>
Line 39, reads "…temperature and pressure sending means…" should read
-- …temperature and pressure sensing means… --.

<u>Column 14,</u>
Lines 23-24, reads "…if the temperature and pressure within said chamber deviates from said…" should read -- …if the temperature and pressure within said chamber deviate from said… --.

UNITED STATES PATENT AND TRADEMARK OFFICE
CERTIFICATE OF CORRECTION

PATENT NO. : 6,984,359 B2
DATED : January 10, 2006
INVENTOR(S) : Florkey et al.

It is certified that error appears in the above-identified patent and that said Letters Patent is hereby corrected as shown below:

<u>Column 16,</u>
Line 20, reads "The method of claim 32 wherein step of purging…" should read -- The method of claim 32 wherein the step of purging… --.
Line 31, reads "…is less than about 132.8 C., and…" should read -- …is less than about 132.8 °C., and… --.
Line 34, reads "…or equal to about 132.8 C." should read -- …or equal to about 132.8 °C. --.

Signed and Sealed this

Sixth Day of June, 2006

JON W. DUDAS
*Director of the United States Patent and Trademark Office*